(12) United States Patent
Nabutovsky et al.

US008868165B1

(10) Patent No.: US 8,868,165 B1
(45) Date of Patent: Oct. 21, 2014

(54) USE OF CARDIOGENIC IMPEDANCE WAVEFORM MORPHOLOGY TO ANALYZE CARDIAC CONDITIONS AND TO ADJUST TREATMENT THERAPY

(75) Inventors: Yelena Nabutovsky, Mountain View, CA (US); Dorin Panescu, San Jose, CA (US); Weiqun Yang, Cupertino, CA (US); Mihir Naware, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1839 days.

(21) Appl. No.: 11/863,516

(22) Filed: Sep. 28, 2007

(51) Int. Cl.
*A61B 5/053* (2006.01)
*A61B 5/04* (2006.01)

(52) U.S. Cl.
CPC .. *A61B 5/053* (2013.01); *A61B 5/04* (2013.01)
USPC .............................. 600/515; 600/547; 607/17

(58) Field of Classification Search
CPC .................................. A61B 5/04; A61B 5/053
USPC ...................... 600/515, 547; 607/17
See application file for complete search history.

(56) References Cited

U.S. PATENT DOCUMENTS

| | | | |
|---|---|---|---|
| 5,609,157 A | 3/1997 | Panescu et al. | |
| 5,630,425 A | 5/1997 | Panescu et al. | |
| 5,779,645 A | 7/1998 | Olson et al. | |
| 6,754,530 B2 | 6/2004 | Bakels et al. | |
| 7,010,347 B2 | 3/2006 | Schecter | |
| 7,082,329 B2 | 7/2006 | Jarverud | |
| 7,751,888 B1 * | 7/2010 | Schecter | 607/17 |
| 2002/0143368 A1 * | 10/2002 | Bakels et al. | 607/9 |
| 2004/0087870 A1 * | 5/2004 | Jarverud | 600/547 |
| 2004/0254613 A1 * | 12/2004 | Ostroff et al. | 607/5 |
| 2005/0043895 A1 * | 2/2005 | Schechter | 702/19 |
| 2005/0215914 A1 * | 9/2005 | Bornzin et al. | 600/508 |
| 2005/0216067 A1 * | 9/2005 | Min et al. | 607/17 |
| 2005/0256545 A1 * | 11/2005 | Koh et al. | 607/17 |
| 2006/0111751 A1 * | 5/2006 | Cazares | 607/14 |
| 2006/0247703 A1 * | 11/2006 | Gutierrez | 607/17 |
| 2007/0288059 A1 * | 12/2007 | Davenport et al. | 607/6 |
| 2008/0177194 A1 * | 7/2008 | Zhang et al. | 600/513 |
| 2010/0179411 A1 * | 7/2010 | Holmstrom et al. | 600/374 |

FOREIGN PATENT DOCUMENTS

EP          1538979 B1     3/2006

* cited by examiner

*Primary Examiner* — Carl H Layno
*Assistant Examiner* — Jennifer Ghand
(74) *Attorney, Agent, or Firm* — Steven M. Mitchell

(57) ABSTRACT

In specific embodiments, one or more cardiogenic impedance signal template is stored, where each template has a corresponding morphology. Additionally, one or more cardiogenic impedance signal is obtained using electrodes implanted within a patient, where each signal has a corresponding morphology. The morphology of one or more obtained cardiogenic impedance signal is compared to the morphology of one or more stored template, to determine one or more metric indicative of similarity between the compared morphologies. The one or more metric indicative of similarity is used to analyze the patient's cardiac condition, to discriminate among arrhythmias and/or to adjust a cardiac pacing parameter.

8 Claims, 14 Drawing Sheets

USE OF CARDIOGENIC IMPEDANCE WAVEFORM MORPHOLOGY TO ANALYZE CARDIAC CONDITIONS AND TO ADJUST TREATMENT THERAPY

CROSS-REFERENCE TO RELATED APPLICATION

This application is related to commonly assigned U.S. patent application Ser. No. 11/558,101, entitled "Systems and Methods to Monitor and Treat Heart Failure Conditions" (Yang et al), filed Nov. 9, 2006, which is incorporated herein by reference.

FIELD OF THE INVENTION

Embodiments of the present invention relate to systems and methods for using cardiogenic impedance (Zc) signal waveform morphology, e.g., to analyze cardiac conditions and/or to adjust treatment therapy.

BACKGROUND

It is known that implanted electrodes can be used to obtain cardiogenic impedance signals, also known as cardiac impedance signals, or simply as impedance waveforms. Such impedance signals have been used, e.g., to determine the occurrence of certain mechanical events, such as, left or right heart valve closure. It would be beneficial if additional uses for cardiogenic impedance signals were provided.

SUMMARY

Embodiments of the present invention relate to methods and systems for analyzing a patient's cardiac condition and/or adjusting treatment therapy, based on one or more cardiogenic impedance signal obtained using electrodes implanted in a patient.

In specific embodiments, one or more cardiogenic impedance signal template is stored, where each template has a corresponding morphology. Additionally, one or more cardiogenic impedance signal is obtained using electrodes implanted within a patient, where each signal has a corresponding morphology. The morphology of one or more obtained cardiogenic impedance signal is compared to the morphology of one or more stored template, to determine one or more metric indicative of similarity between the compared morphologies. The one or more metric indicative of similarity is used to analyze the patient's cardiac condition and/or to adjust a treatment therapy (e.g., adjust a cardiac pacing parameter and/or adjust drug therapy).

In certain embodiments, a cardiogenic impedance signal template indicative of a heart failure condition is stored, and the morphology of such a template is compared to the morphology of at least one obtained cardiogenic impedance signal to produce one or more similarity metric. A change the patient's heart failure condition can be determined based on the similarity metric(s). Further, an alert and/or other response can be triggered in response to detecting an onset of heart failure.

In certain embodiments, a separate cardiogenic impedance signal template is stored for each of a plurality of different heart failure conditions. The morphologies of such templates are compared to the morphology of at least one obtained cardiogenic impedance signal to produce a plurality of similarity metrics, each of which is indicative of similarity between the morphology of the obtained signal and the morphology of a different one of the templates. The patient's heart failure condition can be determining based on which template has a morphology most similar to the morphology of the obtained cardiogenic impedance signal.

In accordance with specific embodiments, a cardiogenic impedance signal template indicative of an arrhythmia is stored. The morphology of such template is compared to the morphology of an obtained cardiogenic impedance signal to produce a similarity metric, and arrhythmia detection and/or arrhythmia discrimination is performed based on the metric. For example, a cardiogenic impedance signal template indicative of supraventricular tachycardia (SVT) can be stored, and its morphology can be compared to the morphology of an obtained cardiogenic impedance signal, to produce a similarity metric. SVT can be detected if the similarity metric exceeds a specific threshold. The patient's heart rate, and/or other criteria, can also be taken into account in such a detection algorithm. For example, if the patient's heart rate exceeds a certain threshold (e.g., 150 beats per minute) and the similarity metric indicates that the morphology of an obtained cardiogenic impedance signal is not similar to the SVT template, then it can be determined that the patient is experiencing VT. In this case, both arrhythmia detection and arrhythmia discrimination are performed.

It's also possible to store a first cardiogenic impedance signal template indicative of supraventricular tachycardia (SVT) and a second cardiogenic impedance signal template indicative of ventricular tachycardia (VT). An obtained cardiogenic impedance signal can be compared to each template to determined a first metric indicative of similarity between the morphology of the obtained signal and the morphology of the first template indicative of SVT, and determine a second metric indicative of similarity between the morphology of the obtained signal and the morphology of the second template indicative of VT. Arrhythmia detection and/or arrhythmia discrimination can be performed based on the first and second metrics. Additionally, a template indicative of a patient's normal sinus rhythm can be compared to an obtained cardiogenic impedance signal to produce a similarity metric, and such similarity can also be used for arrhythmia detection and/or discrimination. Cardiogenic impedance signal templates for other arrhythmias, besides SVT and VT, can also be stored and compared to obtained cardiogenic impedance signals, and similarities therebetween can be used to detect and discriminate between such other arrhythmias.

In accordance with specific embodiments, a cardiogenic impedance signal template indicative of an episode of a disorder (e.g., an ischemic episode) can be stored. The morphology of such a template can be compared to the morphology of an obtained cardiogenic impedance signal, for the purpose of detected episodes of the disorder. It's also possible to store a cardiogenic impedance signal template for each of a plurality of different disorders, so that a plurality of disorders can be monitored for at the same time.

In accordance with specific embodiments, a cardiogenic impedance signal template indicative of a healthy cardiac condition is stored, and a metric indicative of similarity between the morphology of an obtained signal and the morphology of the template indicative of the healthy cardiac condition is determined. Treatment therapy can be adjusted based on the metric, e.g., to attempt to increase similarity. In specific embodiments, one or more cardiac resynchronization therapy (CRT) parameter is adjusted based on the metric, e.g., to attempt to increase the similarity. In other embodiments, drug therapy is adjusted, e.g., to attempt to increase similarity. Additionally, as the comparisons are repeated over time, a change in the patient's cardiac condition can be monitored based on changes in the metric over time.

This description is not intended to be a complete description of, or limit the scope of, the invention. Other features, aspects, and objects of the invention can be obtained from a review of the specification, the figures, and the claims.

DETAILED DESCRIPTION

Figure 1:
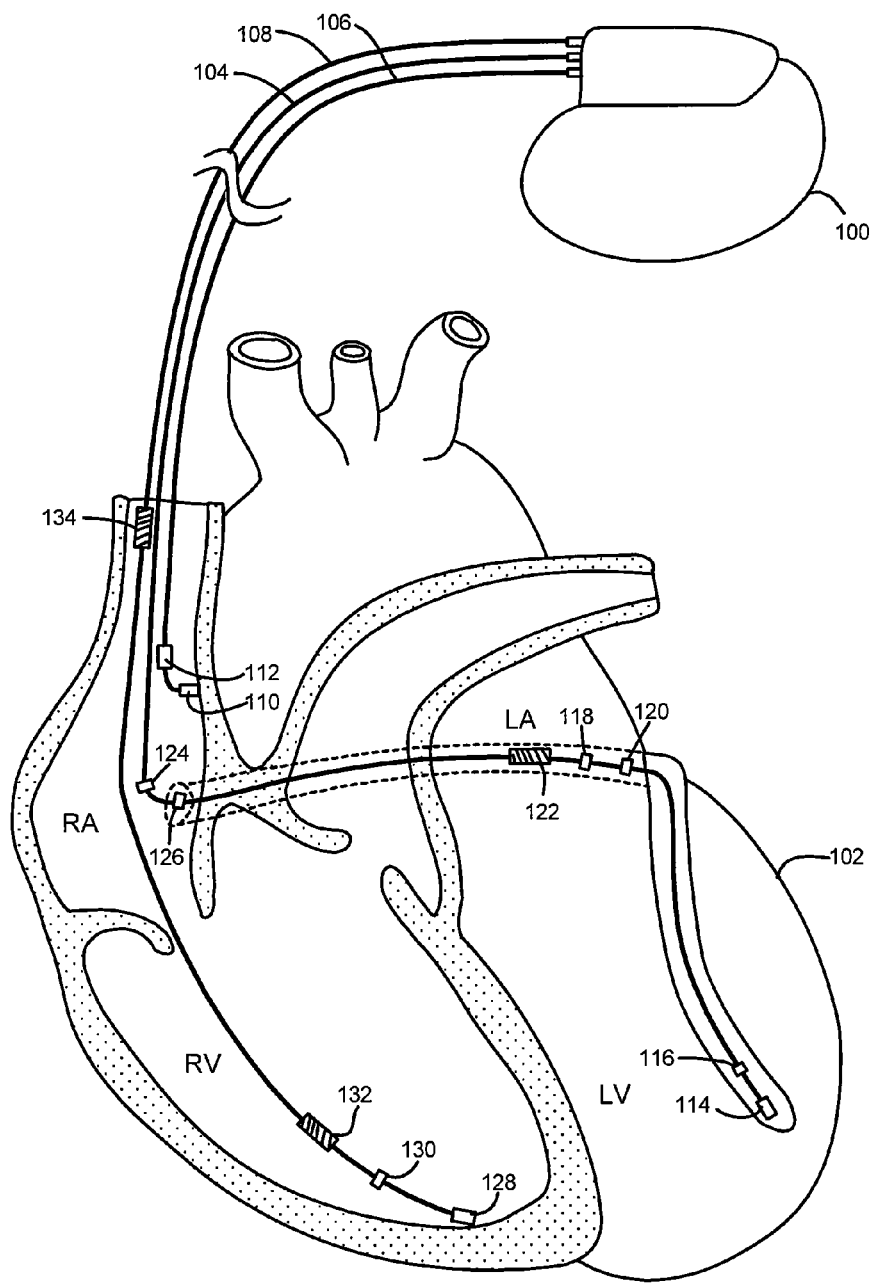
FIG. 1 is a diagram of an exemplary implantable device in relation to a human heart, including leads with electrodes that provide sensing vectors for obtaining cardiogenic impedance waveforms.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

The disclosed systems and methods of the present invention generally relate to systems and methods for using cardiogenic impedance waveform morphology to analyze cardiac conditions and/or to adjust treatment therapy. While it's possible and within the scope of the present invention to employ techniques of the present invention in an external (i.e., non-implantable) system, embodiments of the present invention are especially useful when employed by an implantable cardiac device. Accordingly, an exemplary implantable cardiac device in which embodiments of the present invention are useful is first described with reference to FIGS. 1 and 2.

Exemplary Implantable Device

As shown in FIG. 1, an exemplary implantable medical device ("implantable device" 100), in this case an exemplary implantable cardioverter-defibrillator (ICD), is in electrical communication with a patient's heart 102 by way of three leads, 104, 106 and 108, suitable for sensing, delivering multi-chamber stimulation and shock therapy. Not every configuration has all of the illustrated electrodes, but a given actual configuration may include some of the illustrated electrodes and/or even more electrodes than illustrated.

To sense atrial cardiac signals and to provide right atrial chamber stimulation therapy, the implantable device 100 is coupled to an implantable right atrial lead 106, typically having an atrial tip electrode 110 and an atrial ring electrode 112, which typically is implanted in the patient's right atrial appendage. Implantable device 100 is also known as and referred to as a pacing device, a pacing apparatus, a cardiac rhythm management device, or an implantable cardiac stimulation device. Alternatively, the implantable device 100 could be a defibrillator, or cardioverter, or have combined pacing and defibrillation/cardioversion capabilities.

To sense left atrial and ventricular cardiac signals and to provide left chamber pacing therapy, the implantable device 100 is coupled to a "coronary sinus" lead 104 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 104 is designed to receive atrial and ventricular cardiac signals and to deliver left ventricular pacing therapy using a left ventricular (LV) tip electrode 114 and a LV ring electrode 116. Left atrial pacing therapy uses, for example, first and second left atrial (LA) ring electrodes 118 and 120. Shocking therapy can be performed using at least a left atrial (LA) coil electrode 122. For a description of an exemplary coronary sinus lead, see U.S. Pre-Grant Publication No. 20010050681, "A Self-Anchoring Coronary Sinus Lead" (Pianca et al.), and U.S. Pat. No. 5,466,254, entitled, "Coronary Sinus Lead with Atrial Sensing Capability" (Helland), which patent documents are incorporated herein by reference. Coronary sinus lead 104 may also include a pair of right atrial (RA) ring electrodes 124 and 126, which may be used to provide right atrial chamber pacing therapy.

The implantable device 100 is also shown in electrical communication with the patient's heart 102 by way of an implantable right ventricular lead 108, typically having an right ventricular (RV) tip electrode 128, an RV ring electrode 130, an RV coil electrode 132, and a superior vena cava (SVC) coil electrode 134 (also known as a right atrial (RA) coil electrode). Typically, the right ventricular lead 108 is transvenously inserted into the heart 102 so as to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Cardiogenic impedance measures can be obtained using a single vector, or using multiple vectors simultaneously, quasi-simultaneously, or sequentially using any of the electrodes illustrated in FIG. 1, either in pairs or in combinations of three or more electrodes. For example, a multi-vector network that includes three intracardiac vectors: a vector between the left ventricle (LV) and the right atrium (RA), a vector between the LV and the right ventricle (RV), and a vector between two electrodes in the right ventricle (RV), can be used to obtain a cardiogenic impedance signal. The term multi-vector network as used herein refers to any multi-vector network with two or more vectors between physical, logical, and or virtual electrodes, such as between the physical electrodes illustrated in FIG. 1. A single vector used to obtain a cardiogenic impedance signal can include as few as two electrodes, e.g., a LV ring electrode and a RV ring electrode. These are just a few examples, which are not meant to be limiting.

Figure 2:
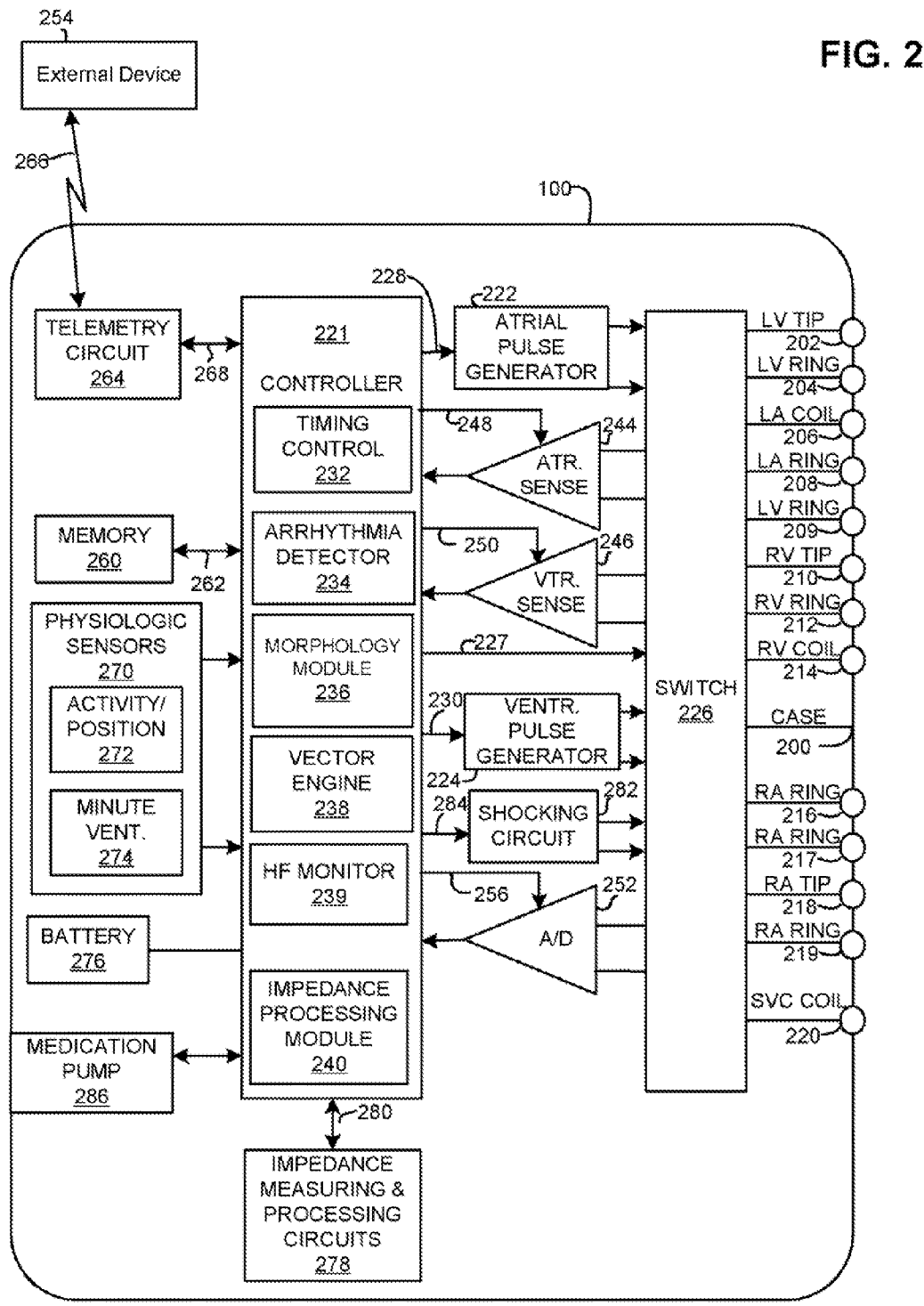
FIG. 2 is a high level block diagram of the exemplary implantable device of FIG. 1, in greater detail.

FIG. 2 shows an exemplary block diagram depicting various components of the exemplary implantable device 100. The components are typically contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 122, 132, 134 for stimulating purposes. The case 200 further includes a connector (not shown) having a plurality of terminals (202, 204, 206, 208, 209, 210, 212, 214, 216, 217, 218, 219, and 220—shown schematically with the names of the electrodes to which they are connected shown next to the terminals), including: a left ventricular tip terminal (LV TIP) 202 for left ventricular tip electrode 114; a left ventricular ring terminal (LV RING) 204 for left ventricular ring electrode 116; a left atrial shocking terminal (LA COIL) 206 for left atrial coil electrode 122; a left atrial ring terminal (LA RING) 208 for left atrial ring electrode 118; a left atrial ring terminal (LA RING) 409 for left atrial ring electrode 120; a right ventricular tip terminal (RV TIP) 210 for right ventricular tip electrode 128; a right ventricular ring terminal (RV RING) 212 for right ventricular ring electrode 130; a right ventricular shocking terminal (RV COIL) 214 for RV coil electrode 132; a right atrial ring terminal (RA RING) 216 for atrial ring electrode 124; a right atrial ring terminal (RA RING) 217 for right atrial ring electrode 126; a right atrial tip terminal (RA TIP) 218 for atrial tip electrode 110; a right atrial ring terminal (RA RING) 219 for atrial ring electrode 112; and a SVC shocking terminal (SVC COIL) 220 for right atrial SVC coil electrode 134.

The exemplary implantable device 100 may include a programmable microcontroller 221 that controls various operations of the implantable device 100, including cardiovascular monitoring, hemodynamic monitoring, and cardiovascular stimulation therapy. Microcontroller 221 includes a microprocessor (or equivalent control circuitry), RAM and/or ROM memory, logic and timing circuitry, state machine circuitry, and I/O circuitry.

The exemplary implantable device 100 may further include an atrial pulse generator 222 and a ventricular pulse generator 224 that generate pacing stimulation pulses for delivery by the right atrial lead 106, the coronary sinus lead 104, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 221, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 221 via appropriate control signals 228 and 230, respectively, to trigger or inhibit the stimulation pulses.

Microcontroller 221 is illustrated as including timing control circuitry 232 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 221 may also implement an arrhythmia detector 234, a morphology detector 236, a vector engine 238, and an impedance processing module 240. The microcontroller 221 may process input from physiological sensors 270, such as accelerometers of an activity/position module 272, and a minute ventilation module 274, etc. The morphology module 236 can be used to detect the morphology of IEGM and/or cardiogenic impedance signals that are obtained using implanted electrodes. The arrhythmia detector 234 can detect arrhythmias based on obtained IEGMs and/or cardiogenic impedance signals, in accordance with embodiments of the present invention. For example, the arrhythmia detector can detect arrhythmias and/or discriminate between arrhythmias, based on the morphology of cardiogenic impedance signals, using embodiments of the present invention described below. The microcontroller 221 can also implement a heart failure (HF) monitor 239, which can monitor and classify heart failure conditions, in accordance with embodiments of the present invention described below.

The components 232, 234, 236, 238, 239 and 240 may be implemented in hardware as part of the microcontroller 221, or as software/firmware instructions programmed into an implementation of the implantable device 100 and executed on the microcontroller 221 during certain modes of operation. Although not shown, the microcontroller 221 may further include other dedicated circuitry and/or firmware/software components that assist in monitoring various conditions of the patient's heart and managing pacing therapies. It also possible that part of, or entire components 232, 234, 236, 238, 239 and 240 can be implemented external to the microcontroller 221, e.g., using dedicated circuitry and/or firmware/software components within the implantable device 100, and/or within an external device (e.g., 254).

Atrial sensing circuits 244 and ventricular sensing circuits 246 may also be selectively coupled to the right atrial lead 106, coronary sinus lead 104, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/ or automatic gain control, bandpass filtering, and a threshold detection circuit to selectively sense the cardiac signal of interest. The automatic gain control enables the exemplary implantable device 100 to sense low amplitude signal characteristics of atrial or ventricular fibrillation.

The outputs of the atrial and ventricular sensing circuits 244 and 246 are connected to the microcontroller 221 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 221 over signal lines 248 and 250 to control, for example, the gain and the timing of blocking circuitry (not shown) optionally coupled to the inputs of the sensing circuits 244, 246.

Cardiac signals, including signals involved in impedance measurements, can be supplied to an analog-to-digital (A/D) data acquisition system 252, which is configured to acquire these signals, convert the raw analog data into a digital signal, and store the digital signals for later processing and/or telemetric transmission to an external device 254. The data acquisition system 252 is coupled to the right atrial lead 106, the coronary sinus lead 104, and the right ventricular lead 108 through the switch 226 to process signals across any pair of desired electrodes.

The data acquisition system 252 is coupled to the microcontroller 221, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 221 detects a depolarization signal during a window following a stimulation pulse, the presence of which indicates that capture has occurred. The microcontroller 221 enables capture detection by triggering the ventricular pulse generator 224 to generate a stimulation pulse, starting a capture detection window using the timing control circuitry 232 within the microcontroller 221, and enabling the data acquisition system 252 via control signal 256 to sample the cardiac signal that falls in the capture detection window and, based on the amplitude, determines if capture has occurred.

The microcontroller 221 is further coupled to a memory 260 by a suitable data/address bus 262. The programmable operating parameters used by the microcontroller 221 are stored in memory 260 and used to customize the operation of the exemplary implantable device 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 102 within each respective tier of therapy. The memory 260 can also store cardiogenic impedance signal templates, in accordance with embodiments of the present invention discussed below.

The operating parameters of the exemplary implantable device 100 may be non-invasively programmed into the memory 260 through a telemetry circuit 264 in telemetric communication via communication link 266 with the external device 254, such as a programmer, local transceiver, or a diagnostic system analyzer. The microcontroller 221 can activate the telemetry circuit 264 with a control signal 268. The telemetry circuit 264 allows intracardiac electrograms, cardiogenic impedance signals and status information relating to the operation of the exemplary implantable device 100 (as contained in the microcontroller 221 or memory 260) to be sent to the external device 254 through an established communication link 266.

The physiological sensors 270 referred to above can further include, for example, "rate-responsive" sensors that adjust pacing stimulation rates according to the exercise state of the patient. Accordingly, the microcontroller 221 responds by adjusting the various pacing parameters (such as rate, etc.) at which the atrial and ventricular pulse generators 222 and 224 generate stimulation pulses.

The physiological sensors 270 may include mechanisms and sensors to detect bodily movement 272, minute ventilation 274, changes in blood pressure, changes in cardiac output, changes in the physiological condition of the heart, diurnal changes in activity (e.g., detecting sleep and wake states), G-force acceleration of the ICD case 200, length of the cardiac QT interval, blood oxygen saturation, blood pH, changes in temperature, respiration rate, and QRS wave duration. While shown as being included within the exemplary implantable device 100, the physiological sensor(s) 270 may also be external to the exemplary implantable device 100, yet still be implanted within or carried by the patient, e.g., a blood pressure probe. Examples of physiological sensors external to the case 200 that may be deployed by implantable device 100 include sensors that, for example, sense respiration activities, O2 saturation, evoked response, pH of blood, and so forth.

The illustrated physiological sensors 270 include one or more activity/position sensors 272 (e.g., 1D or 3D accelerometers, movement sensors, etc.) to detect changes in the patient's position. The activity/position sensors 272 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 274 may also be included in the physiological sensors 270 in order to sense rate and depth of breathing. Minute ventilation can be measured as the total volume of air that moves in and out of a patient's lungs in a minute. The MV sensor 274 may use impedance measuring and processing circuits 278 to sense air movement by measuring impedance across the chest cavity.

The impedance measuring and processing circuits 278 communicate with the microcontroller 221, e.g., via control signals 280 and can be used for obtaining many types of bodily and intracardiac impedances, including a network of single- or multi-vector impedance measurements. Such impedance measurements can be used for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 278 may be coupled to the switch 226 so that any desired electrode may be used, and networks of vectors can be selected by the multi-vector network engine 238. The impedance measuring circuit 278 can also be used to obtain cardiogenic impedance signals that are compared to templates, in accordance with embodiments of the present invention. Additionally, the impedance measuring circuit 278 can be used to obtain cardiogenic impedance signals that are used to produce templates. Exemplary details of impedance measuring and processing circuits 278 are provided in FIG. 10, which is discussed below.

The exemplary implantable device 100 additionally includes a battery 276 that provides operating power to all of the components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 10 A, at voltages above 500 V, for periods of 2-20 microseconds). The battery 276 also desirably has predictable discharge characteristics so that elective replacement time can be detected. As one example, the exemplary implantable device 100 employs lithium/silver vanadium oxide batteries.

The exemplary implantable device 100 can further include magnet detection circuitry (not shown), coupled to the microcontroller 221, to detect when a magnet is placed over the exemplary implantable device 100. A magnet may be used by a clinician to perform various test functions of the exemplary implantable device 100 and/or to signal the microcontroller 221 that an external programmer (e.g., 254) is in place to receive or transmit data to the microcontroller 221 through the telemetry circuits 264.

The microcontroller 221 further controls a shocking circuit 282 via a control signal 284. The shocking circuit 282 generates shocking pulses of low (e.g., up to 0.5 joules), moderate (e.g., 0.5-10 joules), or high energy (e.g., 11-40 joules), as selected by the microcontroller 221. Such shocking pulses are applied to the patient's heart 102 through at least two shocking electrodes selected, for example, from the left atrial coil electrode 122, the RV coil electrode 132, and/or the SVC coil electrode 134. As noted above, the case 200 may act as an active electrode in combination with the RV coil electrode 132, or as part of a split electrical vector using the SVC coil electrode 134 or the left atrial coil electrode 122 (i.e., using the RV coil electrode 132 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 221 is capable of controlling the synchronous or asynchronous delivery of the shocking pulses.

The implantable device can also include a medication pump 286, which can deliver (e.g., titrate) medication to a patient, if triggered to do so. Information regarding exemplary implantable medication pumps may be found in U.S. Pat. No. 4,731,051 (Fischell) and in U.S. Pat. No. 4,947,845 (Davis), both of which are incorporated by reference herein. Delivering medication is an example of delivering treatment therapy.

More generally, the exemplary implantable device 100 can be programmed to stimulate different sets of vascular and cardiac muscles through the same lead/electrode system. The exemplary implantable device 100 can be programmed to vary the output voltage of various pulses to effectively stimulate different muscles of the heart and blood vessels, even though the physical placement of leads and electrodes does not change.

Cardiogenic Impedance Signals

Figure 10:
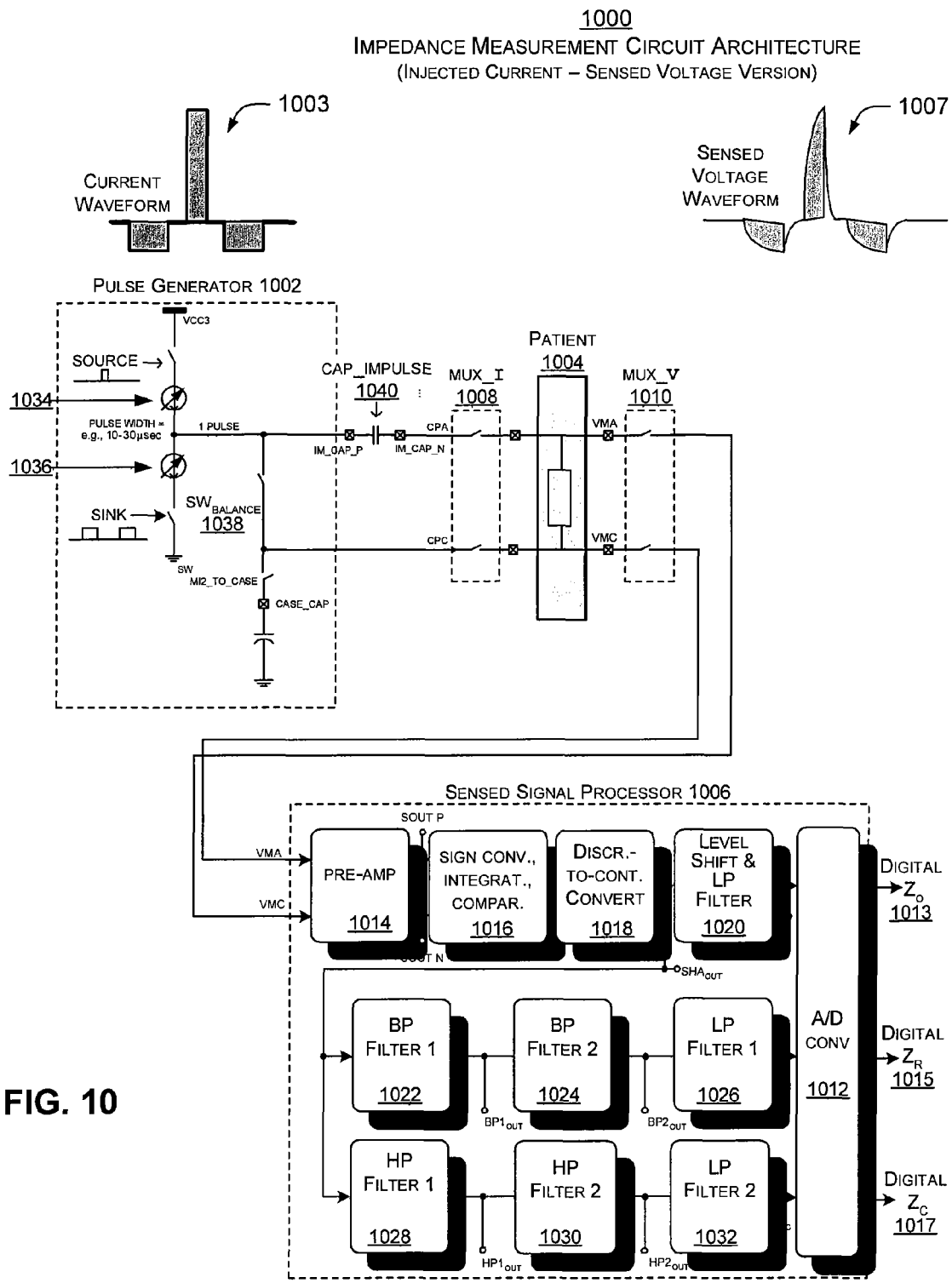
FIG. 10 is a block diagram of an exemplary impedance measuring circuit architecture.
Figure 11:
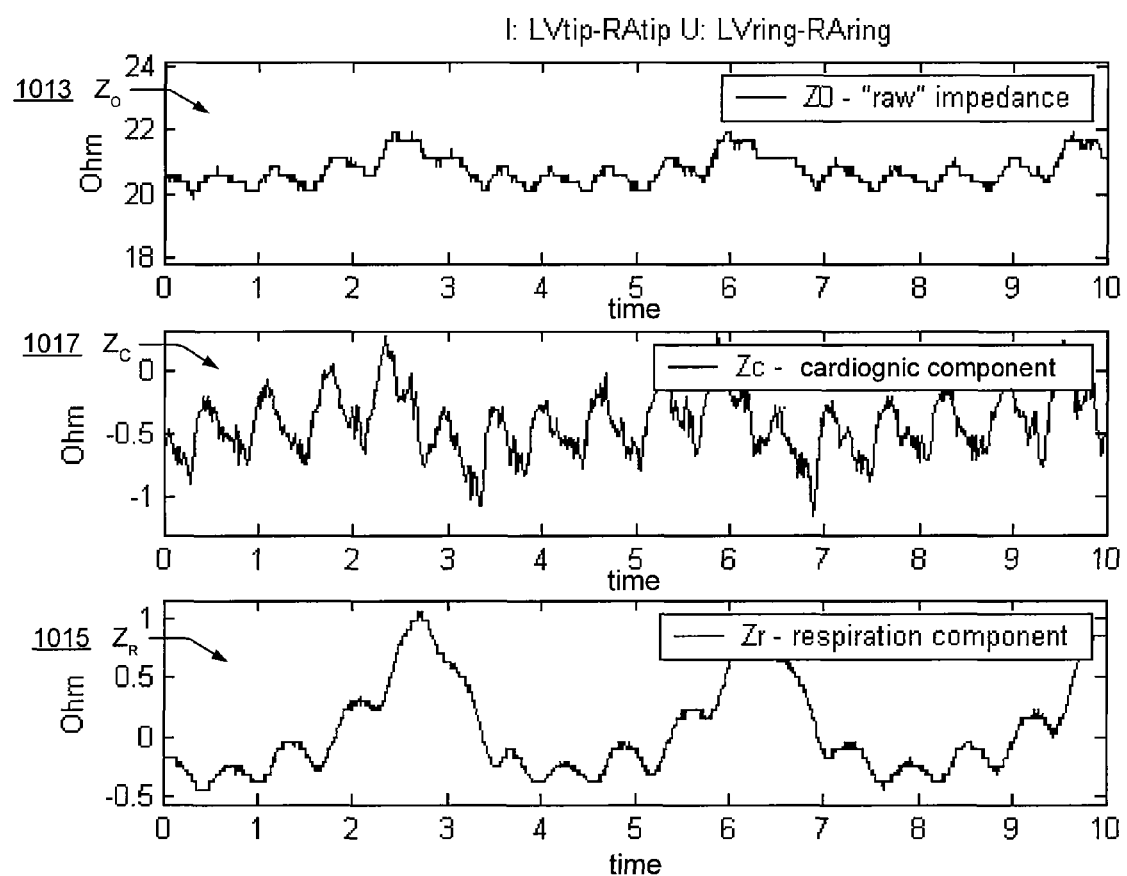
FIG. 11 illustrates exemplary raw, cardiogenic and respirator impedance signals that can be produced using the circuit of FIG. 10.

As shown in FIG. 11, cardiogenic impedance (Zc) signals represent the variation, seen in a raw impedance signals (Zo), which is attributed to the contractile activity of the heart. Similarly, respiratory impedance (Zr) is a component of the raw impedance signal and represents variations caused by respiratory cycles. Signals Zo, Zc and Zr are obtained at the output of the circuit in FIG. 10. Many embodiments of the present rely on the obtaining of cardiogenic impedance signals, and the morphology of such signals. Accordingly, before going into further detail of such embodiments, it would first be useful to explain exemplary techniques for obtaining cardiogenic impedance signals. However, it is noted that embodiments of the present invention are not limited to use with any specific cardiogenic impedance signals, and are not limited to use with any specific techniques for obtaining such signals. Rather, the following description is provided for completeness, so that the reader understands how such signals may be obtained.

The impedance processing module 240 and the impedance measuring and processing circuits 278 can be used to obtain cardiogenic impedance signals. Additionally, the vector engine 238 can assist in selecting electrodes that are use to obtain such signals. The morphology module 236 can be used to compare morphologies of cardiogenic impedance signal templates to cardiogenic impedance signals that are obtained using implanted electrodes, in accordance with embodiments of the present invention described below. Exemplary details of a circuit architecture that can be used to obtain cardiogenic impedance signals is provided below with reference to FIG. 10. Additionally, the waveforms of FIG. 11 are used to explain the differences between raw impedance signals, cardiogenic impedance signals and respiratory impedance signals.

In general, at least a pair of electrodes are used to deliver a stimulation waveform, and at least a pair of electrodes are used to measure the resulting voltage between electrodes, in order to obtain a cardiogenic impedance signal. Such a stimulation waveform preferably should not depolarize the myocardium, should cause only limited battery drain and should have a frequency with an acceptable signal to noise ratio. Exemplary stimulation waveforms, that are useful for obtaining cardiogenic impedance signals, are described in U.S. patent application Ser. No. 11/458,563, entitled "Systems and Methods to Monitor and Treat Heart Failure Conditions", (Yang et al), filed Jul. 19, 2006, which was incorporated herein by reference above, and in U.S. patent application Ser. No. 11/684,664, entitled "Tissue Characterization Using Intracardiac Impedances with an Implantable Lead System", (Wong et al), filed Mar. 12, 2007, which is also incorporated herein by reference. As explained in U.S. patent application Ser. No. 11/458,563 (Yang et al), single- or multi-vector stimulation and sensing vectors can be used to obtain cardiogenic impedance signals. Additionally, as explained in U.S. patent application Ser. No. 11/458,563 (Yang et al), the electrode configurations for measuring cardiogenic impedance, e.g., across a pathway of bodily tissue, can be bipolar (a two node measurement), tripolar (a three node measurement), or quadpolar (a four node measurement), but are not limited thereto. The Yang et al patent application also provides exemplary details of the impedance measuring and processing circuits 278, which can include, e.g., multiplexers and/or other switches, amplifiers, a signal conversion and integration module, a discrete-to-continuous signal conversion module, a level shift and low pass filter, various bandpass, low pass and high pass filters, and an analog-to-digital converter. However, less, alternative and/or additional components can be used.

As mentioned above, a single stimulation vector or multi-vector stimulation network and a single- or multi-vector sensing network can be used to deliver stimulation waveform(s) and obtain one or more cardiogenic impedance signal. Electrodes of conventional implantable lead systems and/or custom lead systems can be used to provide such stimulation and sensing networks. Exemplary electrodes of such leads were discussed above, with references to FIGS. 1 and 2.

Preferred Embodiments

Figure 3:
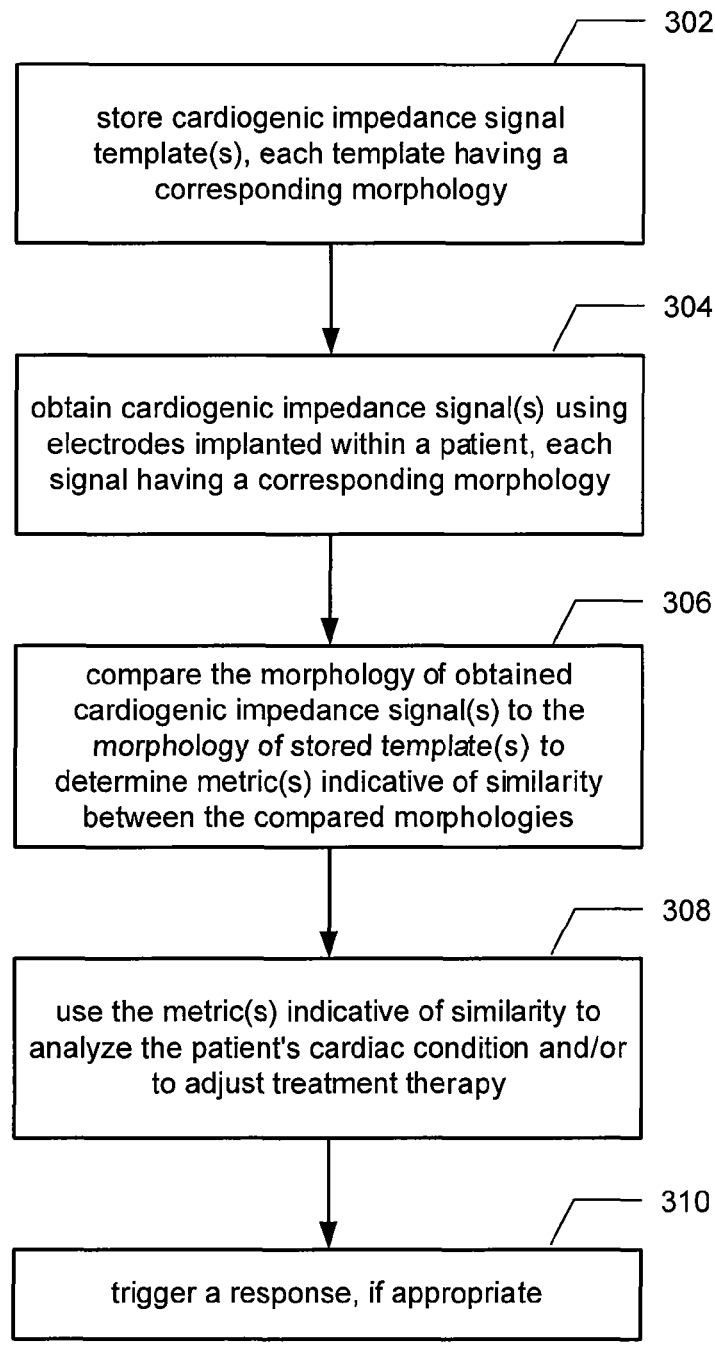
FIG. 3 is a high level flow diagram that is used to explain various embodiments of the present invention.

The high level flow diagram of FIG. 3 will now be used to summarize various embodiments of the present invention. In this flow diagram, and other flow diagrams presented herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of an implantable device and/or an external device. Those skilled in the art may readily write such a control program based on the flow diagrams and other descriptions presented herein.

Referring to FIG. 3, at step 302, one or more cardiogenic impedance signal template is stored, where each template has a corresponding morphology. Such templates can be stored, e.g., in memory 260 of the implantable device 100. As will be described in additional detail below, a template can be representative of an expected cardiogenic impedance signal's morphology during heart failure, during an arrhythmia, during an ischemic episode, etc. Such templates can be patient specific, or determined based on measurements from a broader population. Each template can be representative of a possible cardiogenic impedance signal morphology during a single cardiac cycle, or during a plurality of cardiac cycles. In other words, a width of a template waveform can correspond to a single cardiac cycle, or a template waveform can span more than one cardiac cycle.

Template acquisition may be performed either automatically or with user supervision. Templates are preferably acquired on a patient-by-patient basis because of variability in cardiogenic impedance waveforms due to inter-individual variability and differences in the type and location of stimulation and sensing electrodes. Depending upon the purpose of the template, templates may be acquired during normal sinus rhythm or obtained from stored episode data, e.g., from spontaneous SVTs, VTs other identified heart rhythms as desired.

It is also possible to obtain patient specific templates by pacing or other stimulation that simulates a specific arrhythmia or condition. For example, since it is known that a patient's left atrial pressure (LAP) increases as a patient's heart failure condition progresses, a patient's LAP can be temporarily increased, e.g., by having the patient perform a valsalva maneuver, and corresponding cardiogenic signal information can be obtained and stored, and used to produce one or more template indicative of a heart failure condition. For another example, a patient's right atrium can be paced at a high rate, e.g., 150 beats per minute (bpm), to simulate SVT, and corresponding cardiogenic signal morphology information can be obtained and stored, and used to produce one or more template indicative of SVT. For a further example, a patient's right ventricle can be paced at a high rate, e.g., 180 bpm, to simulate VT, and corresponding cardiogenic signal morphology information can be obtained and stored, and used to produce one or more template indicative of VT. Templates can be based on a single cycle of a cardiogenic signal, or based on an average (e.g., ensemble average) of a plurality of cycles. Stated another way, templates can correspond to a single cardiac cycle, an average over several cardiac cycles, or a series of cardiac cycles.

It is also possible and useful to obtain one or more baseline signal template at implant, or preferably after lead maturation, which can take up to 4 to 6 weeks. Such baseline template(s) may, or may not, correspond to a patient's normal sinus rhythm. Alternatively, or additionally, baseline template(s) can correspond to a patient's initial physical condition and/or disease state. Baseline templates can correspond to a single cardiac cycle, an average over several cardiac cycles, or a series of cardiac cycles.

At step 304, one or more cardiogenic impedance signal is obtained, using electrodes implanted within a patient, where each signal has a corresponding morphology. Exemplary details for obtaining a cardiogenic impedance signal were described above. However, alternative techniques for obtaining cardiogenic impedance signals are also within the scope of the present invention.

At step 306, the morphology of one or more obtained cardiogenic impedance signal is compared to the morphology of one or more stored template, to determine one or more metric indicative of similarity between the compared morphologies. Metrics indicative of similarity are also referred to herein interchangeably as "similarity metrics". Embodiments of the present invention are not limited to use of any specific types of morphology comparison techniques. For example, template matching (also known as pattern matching) or correlation functions can be used. Some template matching or correlation functions align a portion of a signal with a corresponding template and measure the difference in areas under the waveforms. The difference in areas can be a metric indicative of similarity, where the less the difference in areas, the greater the similarity. Alternatively, a percentage match score can be assigned, which is proportional to the difference. Other techniques for comparing waveform morphologies include, but are not limited to, the use of mean square error algorithms and cross correlation or template-matching based finite impulse response (FIR) filters. Other known or future developed morphology comparison techniques can be used.

The length of each cycle of a cardiogenic impedance signal depends on a patient's heart rate/RR interval. Thus, it may be appropriate to stretch, compress, or adjust (or otherwise normalize) template(s) and/or signal(s) obtained at step 304, before the morphologies of templates and obtained signals are compared to determine their similarity. It may also be appropriate to normalize the amplitude of a template and/or an obtained cardiogenic impedance signal, prior to a comparison of morphologies.

At step 308, one or more determined metric indicative of similarity is used to analyze the patient's cardiac condition and/or to adjust treatment therapy. Analyzing the patient's cardiac condition can include, but is not limited to, determining a change in the patient's heart failure status, performing arrhythmia discrimination, performing arrhythmia detection and/or detecting episodes of a disorder. Adjusting treatment therapy can include, e.g., adjusting a cardiac pacing parameter and/or adjusting drug therapy, which can include alerting a patient to adjust their medication or to visit a physician to get their medication adjusted. Adjusting a cardiac pacing parameter can include, but is not limited to, adjusting one or more cardiac resynchronization parameter. Adjusting drug therapy can include titrating a drug and/or adjusting an amount of a drug that is being tritrated or otherwise delivered. Various different types of responses can be triggered, if appropriate (besides adjusting a CRT parameter), as indicated at step 310. In certain embodiments, e.g., where therapy is being adjusted, steps 308 and 310 may be thought of as a single step.

In accordance with certain embodiments, the template(s) are stored within the same implantable device (e.g., 100) that is obtaining the cardiogenic impedance signal(s) to which the template(s) will be compared. In such embodiments, the morphology comparisons can be performed by the implantable device, and the analysis and/or adjustment of step 308 can be performed by the implantable device. Additionally, a response that may be triggered at step 310 can also be preformed by the implantable device. Alternatively, some of the above functions can be performed by an external device (e.g., 254) that communicates with the implantable device (e.g., using telemetry). For example, its possible that one or more cardiogenic impedance template is stored by an external device, and that data for a cardiogenic impedance signal obtained by an implantable device is transmitted to the external device, and that morphology comparisons and the other steps are performed by the external device. In still other embodiments, morphology comparisons can be performed by an implantable device, and similarity metrics can be transmitted from the implantable device to an external device, and the external device can perform analysis and/or control the adjustment of treatment therapy, based on the metrics, and/or trigger specific responses when appropriate (e.g., trigger a patient alert and/or physician alert). These are just a few possibilities for how various steps can be distributed among an implantable device and an external device. Other variations are also possible, and within the scope of the present invention.

The cardiogenic impedance signals(s) obtained at step 306 may be susceptible to activity (e.g., motion) and/or posture changes. Accordingly, the techniques described with reference to FIG. 3 an the FIGS. discussed below can be used in conjunction with an activity and/or position sensor (e.g., 272). For example, it's possible that there are different templates for different posture positions, so that when morphology comparisons are performed, a patient's posture is taken into account, and an appropriate template(s) is/are used when morphologies are compared. It is also possible that morphology comparisons are only performed when the patient has a certain posture (e.g., supine). In certain embodiments, if an activity sensor indicates that the patient is active, morphology comparisons will not be performed. In other embodiments, depending on the purpose of the morphology comparisons, patient activity is gauged based on heart rate, and certain morphology comparisons are only performed when the patient's heart rate is below a certain threshold (this would not be practical if a purpose of the morphology comparison was to detect a tachyarrhythmia). In still other embodiments, if a patient's RR intervals vary by more than a specified percentage, morphology comparisons are not performed. Combinations of these various embodiments are also possible.

Steps 304-310 can be repeated over time. For example, these steps can be performed substantially continuously, periodically (e.g., every minute, hour, day, etc.), or aperiodically (e.g., in response to specific triggering events). In accordance with specific embodiments, data indicative of the similarity metrics determined at step 306 and/or the results of any analysis performed at step 308 are saved for later further analysis and/or trending. Such data can be stored, e.g., in memory 260 of device 100. It's also possible, and likely, that stored templates can be updated from time-to-time, automatically and/or during visits to a physician's office.

Figure 4:
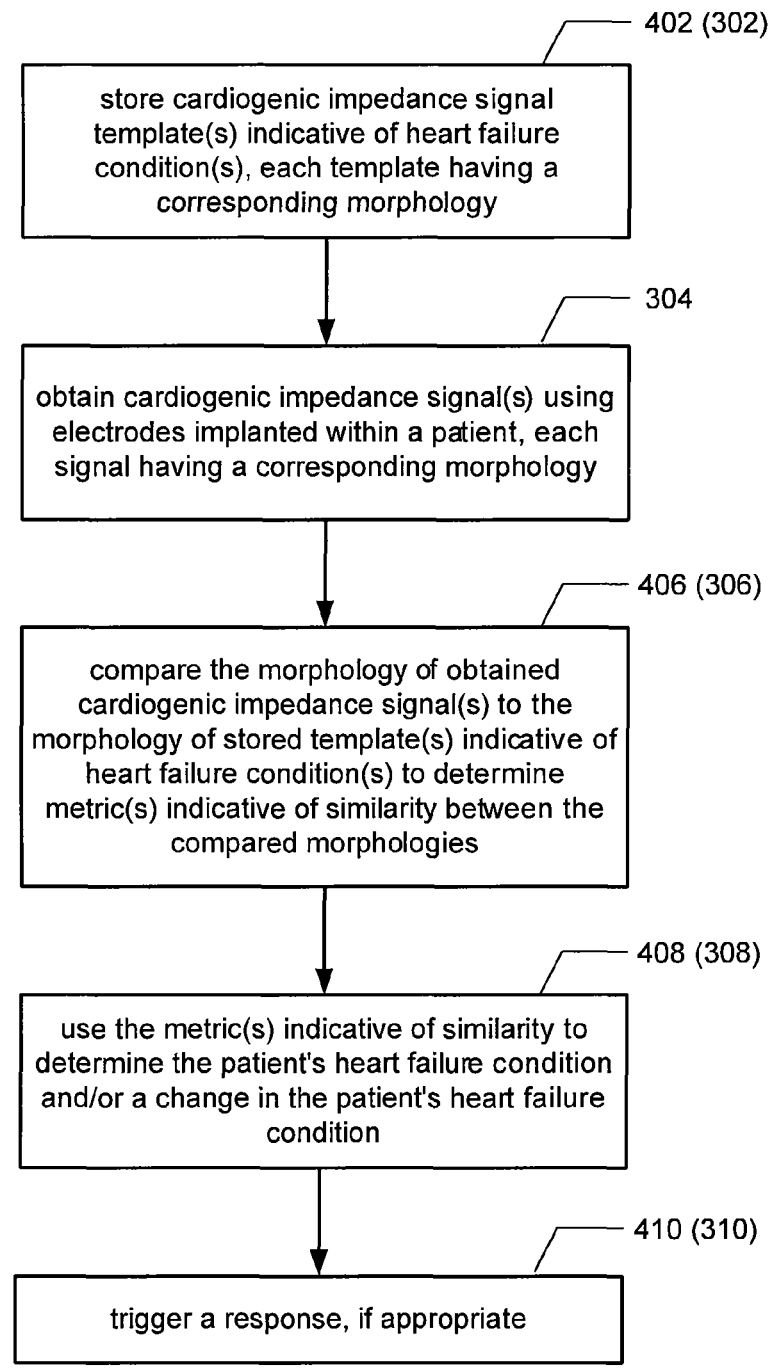
FIG. 4 is a high level flow diagram that is used to explain specific embodiments of the present invention, which are used to monitor a patient heart failure condition and/or changes therein.

Additional details of steps 302, 306, 308 and 310 will be discussed with below reference to FIGS. 4-9. More specifically, FIGS. 4, 6, 8 and 9 are flow diagrams that provide additional details of many of the steps introduced in FIG. 3. In each of these FIGS., where a reference number is shown adjacent another reference number that is in parentheses, the step identified by the reference number is a specific embodiment of the step identified by the reference number in parentheses. For example, in FIG. 4, where a step is identified as "402 (302)", this means that step 402 introduced in FIG. 4 is a specific embodiment of the step 302 previously introduced in FIG. 3. Where a step in FIGS. 4, 6, 8 and 9 is identified with a reference number introduced and discussed earlier, i.e., with reference to an earlier FIG., then that step is the same as the step discussed with reference to the earlier FIG. For example, step 304 in FIGS. 4, 6, 8 and 9 is the same as step 304 in FIG. 4, and thus, that step need not be discussed in detail repeatedly. Rather, the reader should reference the discussion of the earlier FIG.

It is noted that when a stored template is compared to an obtained cardiogenic impedance signal, the template should be appropriate for the electrodes used to obtain the cardiogenic impedance signal. For example, presume that templates are patient specific, and that one of the templates corresponds to a patient's normal sinus rhythm. Also presume that the normal sinus rhythm template was determined based on a cardiogenic impedance signal obtained using a specific pair of electrodes. That template should be compared to later obtained cardiogenic impedance signals obtained using the same specific pair of electrodes, because the morphology of cardiogenic impedance signals are dependent upon which electrodes are used to obtain the signals, and where such electrodes are located.

It is also noted that because multiple cardiogenic impedance signals can be obtained at step 304 (e.g., simultaneously, quasi-simultaneously, or sequentially), with each cardiogenic impedance signal being obtained using a different sensing vector (i.e., a different set of electrodes), templates can be stored for each sensing vector. For example, if three separate cardiogenic impedance signals are obtained at step 304 (using three separate sensing vectors), then a separate template for a same specific condition or rhythm (e.g., for the patient's normal sinus rhythm) can be stored for each sensing vector. In other words, three templates indicative of the patient's normal sinus rhythm may be stored, where each template corresponds to a different sensing vector. In such a case, each cardiogenic impedance signal obtained at step 304 should be compared to its appropriate template(s), and a similarity metric can be determined for each comparison that is performed. Such multiple similarity metrics can be combined into a single similarity score, or used separately, as desired. For another example, three templates indicative of SVT may be stored, where each template corresponds to a different sensing vector.

One or more threshold can be used at step 308. For example, a similarity metric can be compared to a threshold, to determine whether or not a significant change in morphology occurred, or whether a signal is similar enough to a template for a detection to occur. For example, if a similarity score is above a threshold, then a specific detection can occur, but if the similarity score is below a threshold, then the detection does not occur. Multiple such thresholds can be used. For example, where there are two thresholds, a specific action that is taken can depend on where a similarity score falls. Where multiple similarity metrics are determined, e.g., because multiple comparisons are made, there can be one or more threshold for each determined similarity metric. Accordingly, the analysis and/or adjustment performed at step 308 can be based on multiple determined similarity metrics, each of which can been used in an analysis and/or adjustment in a unique manner.

It is noted that metrics of dissimilarity are indeed metrics of similarity, because metrics of dissimilarity are indicative of how similar a template and a signal are. For example, a very low dissimilarity can be indicative of a high similarity, and vice versa.

The high level flow diagram of FIG. 4 will now be used to explain specific embodiments of the present invention, which are used to monitor a patient's heart failure condition and/or changes therein. Referring to FIG. 4, at step 402, which is a specific embodiment of step 302, a cardiogenic impedance signal template indicative of a heart failure condition is stored.

Still referring to FIG. 4, at step 304, one or more cardiogenic impedance signal is obtained, using electrodes implanted within a patient, where each signal has a corresponding morphology, as was explained above with reference to FIG. 1-3.

At step 406, which is a specific embodiment of step 306, the morphology of a cardiogenic impedance signal (obtained at step 304) is compared to the morphology of the template indicative of the heart failure condition (stored at step 402), to determine a metric indicative of similarity of the morphologies.

At step 408, which is specific embodiment of step 308, the patient's heart failure condition and/or a change in the patient's heart failure condition is determined based on the metric.

Assume the template stored at step 402 is indicative of a healthy heart (i.e., when the patient does not have heart failure), and the metric determined at step 406 is indicative of a very high similarity, there can be a determination at step 408 that the patient's heart failure condition did not significantly change, and the heart is healthy. On the other hand, if the metric determined at step 406 is indicative of a low similarity, then there can be a determination at step 408 that the patient's heart failure condition significantly changed, and the patient's heart failure condition worsened. It is also possible that the template stored at step 402 is indicative of an initial cardiac condition (which may or may not correspond to the healthy heart, and which may or may not be indicative of a heart failure condition), and that the metric of similarity determined at step 406 is used to monitor changes (e.g., trends) in the cardiac condition (e.g., changes in a heart failure condition).

Multiple templates can be stored at step 402, where at least one template is indicative of a healthy heart, and one or more further template is indicative of a state or class of heart failure.

The morphology of a signal obtained at step 304 can be compared to the morphology of multiple templates at step 406, and a separate metric indicative of similarity can be determined for each template. In such embodiments, the patient's heart failure condition can be determined by determining which template is most similar to the signal obtained at step 304. For example, if it is determined that the cardiogenic signal obtained at step 304 is most similar to the template indicative of a poor heart failure condition, then it can be determined at step 408 that the patient has a poor heart failure condition. Even further templates can be stored at step 402, so that at least one template exists for each one of numerous different heart failure conditions, to thereby enable ever further levels of heart failure conditions to be determined at step 408. For a specific example, at least one template can be stored for each of a plurality of different heart failure classifications, e.g., such as New York Heart Association (NYHA) classes I, II, III and IV. It also possible to store one or more template indicative of left side heart failure and one or more template indicative of right side heart failure.

Still referring to FIG. 4, an appropriate response can be triggered at step 410, based on the determination of step 408. For example, an alert could be triggered. The alert can be a vibratory or auditory alert that originates from within the implantable device 100. Alternatively or additionally, the implantable device 100 may wirelessly transmit an alert to an external device (e.g., 254) that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible an arrhythmia may be avoided, or if it does occur, the patient will be less dangerous to themselves and others if the patient is resting when the arrhythmia occurs (as opposed, e.g., to driving a car). It is also possible that the alert can be generated by an external device (e.g., 254). Therapy for treating heart failure can also be triggered and/or adjusted at step 410.

Additionally or alternatively, the patient can be instructed to take medication when alerted. Additionally or alternatively, a caregiver (e.g., physician) can be alerted if it is determined that the patient is experiencing an acute heart failure exacerbation. Additionally or alternatively, information related to the patient's cardiogenic impedance signal morphology, IEGM morphology, similarity metric(s), etc. can be stored. If such information is stored in an implanted device, such information can be continually, or from time to time, automatically uploaded to an external device (e.g., 254). Such an external device 254 can be located, e.g., in the patient's home, and the information can be transmitted (e.g., through telephone lines or the Internet) to a medical facility where a physician can analyze the information. For example, the external device 254 can be a bedside monitor, or an ambulatory device that the patient carries with them. Alternatively, the external device 254 can be an external programmer located at a medical facility, and the information can be uploaded when the patient visits the facility.

Figure 5A:
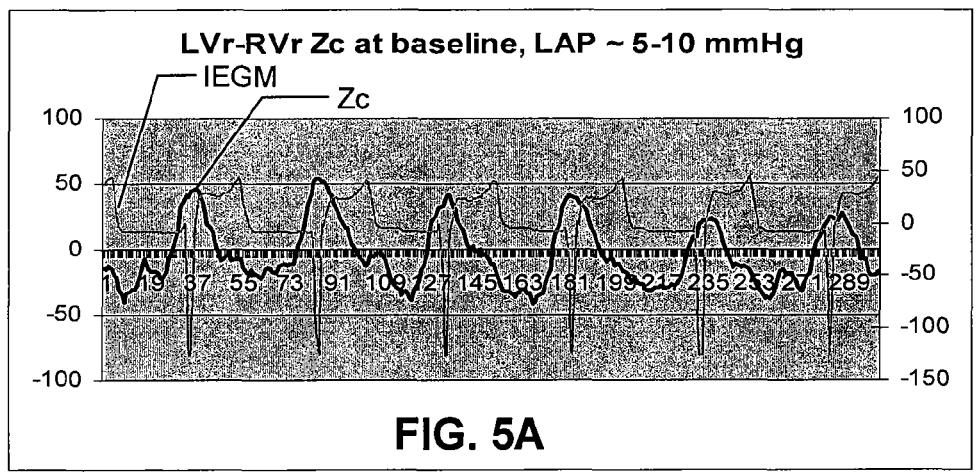
FIG. 5A illustrates the morphology of an exemplary cardiogenic impedance signal obtained for a healthy heart.
Figure 5B:
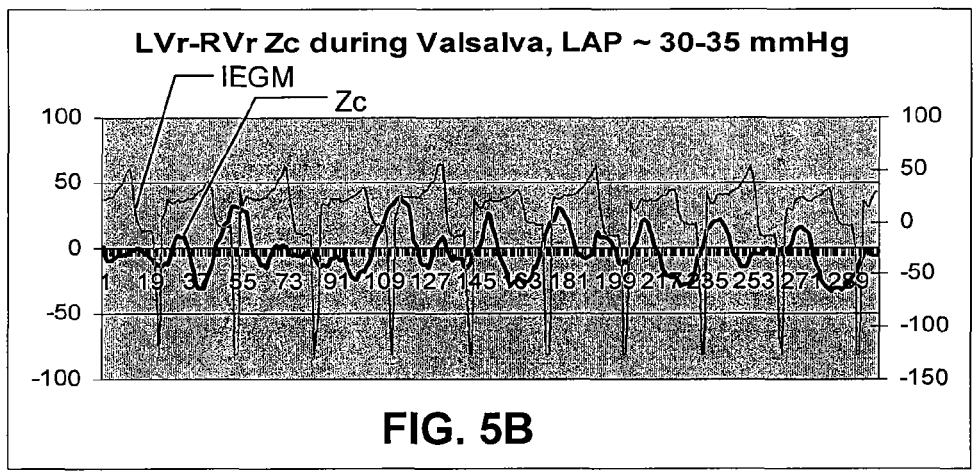
FIG. 5B illustrates the morphology of exemplary cardiogenic impedance signal obtained during a simulated heart failure condition.

The graph of FIG. 5A illustrates an exemplary intracardiac electrogram (IEGM) signal and a corresponding exemplary cardiogenic impedance (Zc) signal obtained for a subject having a relatively low left atrial pressure (LAP) between about 5 and 10 mmHg. In contrast, FIG. 5B illustrates an IEGM signal and a corresponding Zc signal when the same subject's LAP was raised to between about 30 and 35 mmHg using a valsalva maneuver. The same sensing vector, including a left ventricular ring electrode and a right ventricular ring electrode, was used to obtain the Zc signals in FIGS. 5A and 5B. As explained above, when a patient's heart failure condition worsens, the patient's LAP will increase. Thus, the Zc signal of FIG. 5B is intended to simulate the subject's Zc when the subject's heart failure worsens. At step 402, a template representative of a portion (e.g., cycle) of the Zc signal of FIG. 5A can be stored and/or a template representative of a portion of the Zc signal of FIG. 5B can be stored, and at step 406 a Zc signal obtained at step 304 using the same sensing vector can be compared to such template(s) to determine one or more similarity metric. At step 408 the patient's heart failure condition can be determined (e.g., classified), or changes in the condition can be determined, based on the similarity metric(s), and a response may be triggered at step 410.

Figure 5C:
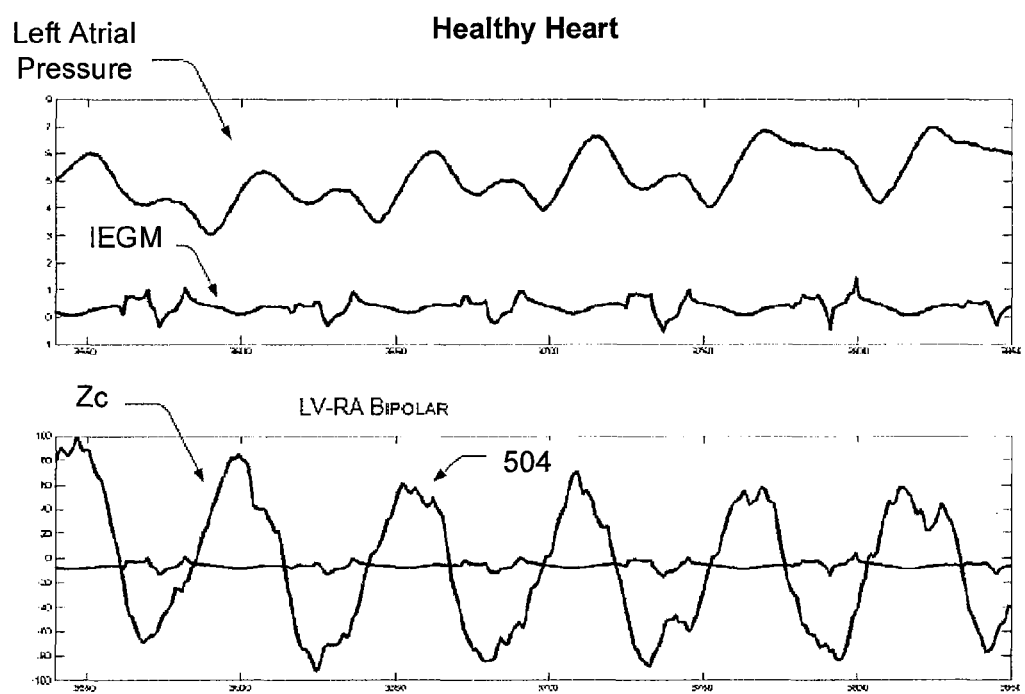
FIGS. 5C-5E illustrate the morphology of additional cardiogenic impedance signals during a normal health condition and during different stages of heart failure.
Figure 5D:
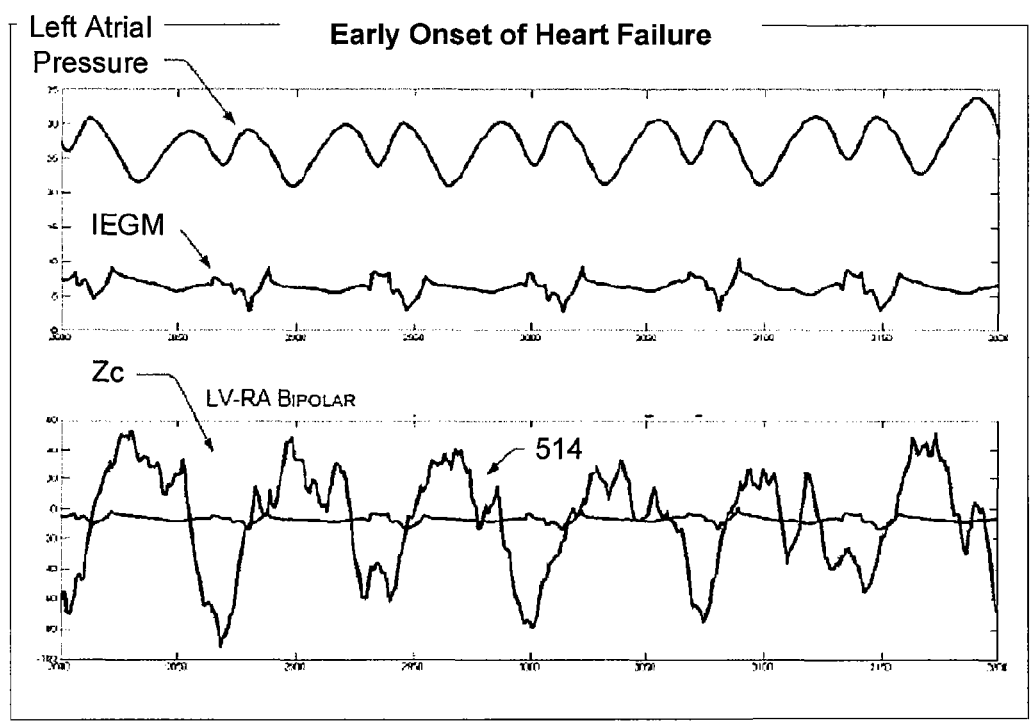
Figure 5E:
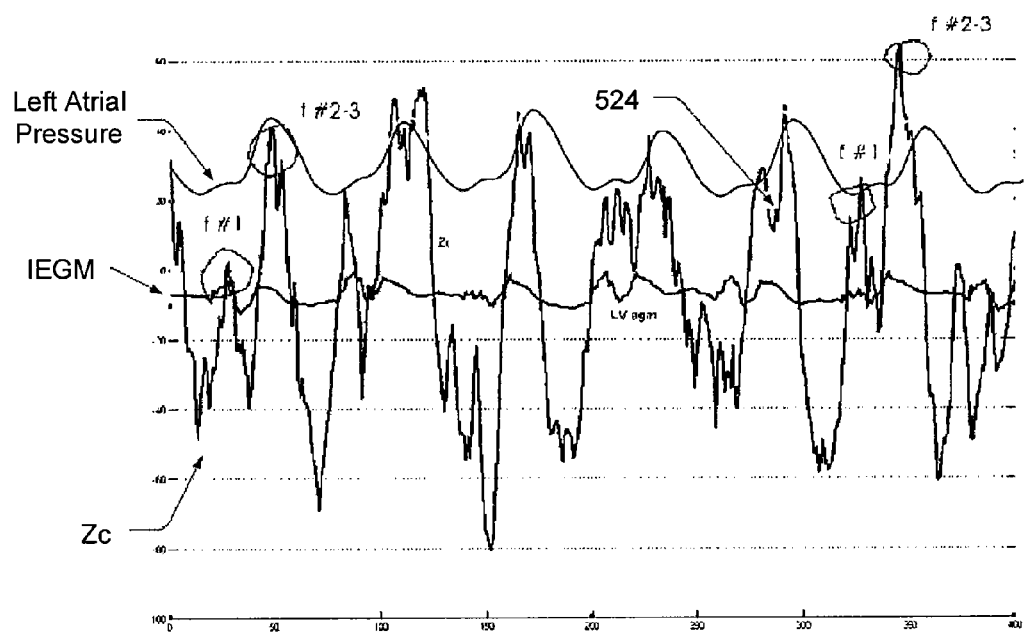

FIGS. 5C, 5D and 5E show additional cardiogenic impedance signals and their relationship to left atrial pressure (LAP) during a patient's cardiac cycle. LAP is known to be a reliable predictor of heart failure progression, as mentioned above. Increasing LAP levels are known to be indicative of worsening heart failure conditions. The intracardiac impedance is sensed over a vector, e.g., between the left ventricle (LV) and the right atrium (RA). (Other vectors can be used.) FIG. 5C shows cardiogenic impedance under normal healthy conditions. Thus the cardiogenic impedance signal of FIG. 5C may be useful for producing a template, indicative of a normal healthy cardiac condition. FIG. 5D shows the intracardiac impedance at the early onset of heart failure. FIG. 5E shows the intracardiac impedance during late heart failure conditions. The cardiogenic impedance signals of FIGS. 5D and 5E can also be used to produce corresponding templates.

In FIG. 5C, for a normal patient free of heart failure, the characteristic morphology of the cardiogenic impedance Zc signal shows relatively smooth waves that follow the cardiac cycle, with relatively little raggedness (i.e., "fractionation") at the crest 504 of each impedance trace peak (or trough). In FIG. 5D, during early onset of heart failure, the Zc signal develops a characteristic morphology of notches 514 in or near the crests—i.e., a moderate degree of fractionation—that may be diagnostic of this stage of heart failure. In FIG. 5E, during late heart failure conditions, the Zc signal develops a characteristic morphology of high volatility and fractionation, where the magnitude of the notches 524 increases significantly and their frequency of occurrence is high.

For example, in FIG. 5E, features labeled f#1 are seen mostly around the P wave of the cardiac cycle. Features #2 and #3 are separated by a notch that occurs near the T wave of the cardiac cycle. Feature #2 precedes the notch, whereas feature #3 follows it. These features are not seen in a normal LV-RA cardiogenic impedance waveform, such as that shown in FIG. 5C. The frequency of occurrence of these features (e.g., notches indicative of a fractionated waveform) increases as the average LAP increases from normal (FIG. 5C), to elevated (FIG. 5D), to very high late heart failure levels (FIG. 5E). Thus, the morphology of the obtained cardiogenic impedance signal can accurately stage heart failure, and notably can predict or determine the early onset of heart failure.

With therapy, as the LV-RA cardiogenic impedance resolves back from the fractionated morphology in FIG. 5E to the normal morphology in FIG. 5C, the resolution indicates that the LA and/or LVED pressures decrease towards normal values. Such therapy (e.g., delivered at step 410) can include, e.g., adjusting the A-V or V-V timing delay such that the morphology of the LV-RA vector impedance trends back from that shown in FIG. 5E to that in FIG. 5C. This can be achieved using one of many different techniques. For example, the peaks or troughs seen in the impedance morphology of FIG. 5E can be counted. When the frequency of occurrence of these peaks and troughs is high, the A-V or V-V timing is adjusted from a set value (determined, for example, at implant time) to lower or higher values, with the goal of decreasing the frequency of the feature's occurrence.

In one implementation, timing adjustment(s) is/are made in one direction, for example from original AV and/or V-V timing delays to higher values. If this adjustment results in a decreased frequency of occurrence for the peaks and troughs shown in FIGS. 5D and 5E, then the adjustment is continued in this direction until the LV-RA impedance waveform trends close to normal morphologies, as shown in FIG. 5C. Otherwise, the direction of the timing delay adjustment is reversed and values are decremented from initial settings to lower numbers. Alternatively, other impedance characteristics (as will be described below), or other vectors that correlate with LA and LVED pressures, such as peak-to-peak amplitudes, can be used to adjust the A-V and V-V timing. Additionally, or alternatively, timing delays and drug therapy can be adjusted to increase the similarity of the morphology of an obtained cardiogenic impedance signal and the morphology of the signal shown in FIG. 5C. In other words, the signal shown in FIG. 5C, or portion or average thereof, can be used to produce a template indicative of a healthy cardiac condition.

Figure 6:
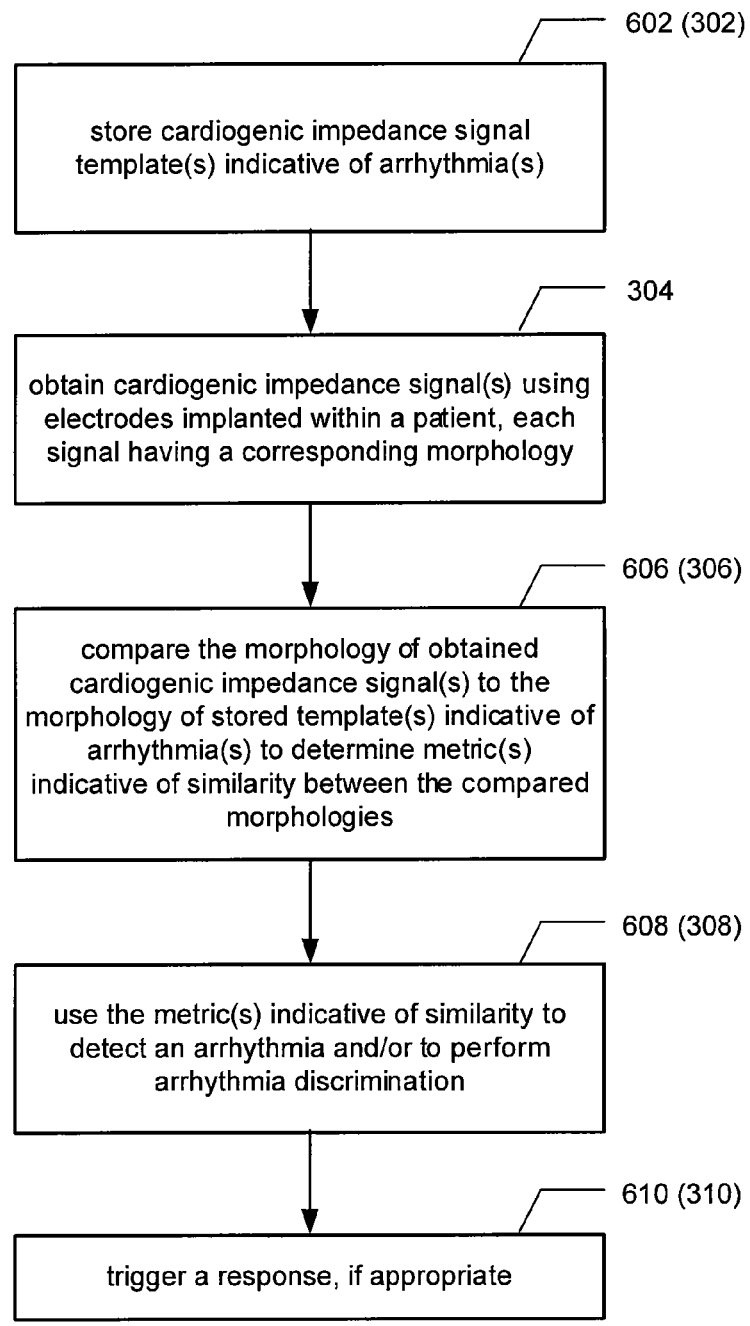
FIG. 6 is a high level flow diagram that is used to explain specific embodiments of the present invention, which are used to detect an arrhythmia and/or perform arrhythmia discrimination.

The high level flow diagram of FIG. 6 will now be used to explain specific embodiments of the present invention, which are used to detect an arrhythmia and/or perform arrhythmia discrimination. Referring to FIG. 6, at step 602, which is a specific embodiment of step 302, one or more cardiogenic impedance signal template indicative of an arrhythmia can be stored. For example, a template indicative of supraventricular tachycardia (SVT) can be stored. Additionally, or alternatively, a cardiogenic impedance signal template indicative of ventricular tachycardia (VT) can be stored. If multiple sensing vectors are used to obtain multiple cardiogenic impedance signals at step 304, then a template indicative of SVT can be stored for each sensing vector, and/or a template indicative of VT can be stored for each sensing vector. At step 606, which is a specific embodiment of step 306, one or more similarity metric is determined. At step 608, which is a specific embodiment of step 308, the metric(s) determined at step 606 can be used to detect an arrhythmia and/or to perform arrhythmia discrimination. At step 610, which is a specific embodiment of step 310, an appropriate response can be triggered.

Figure 7A:
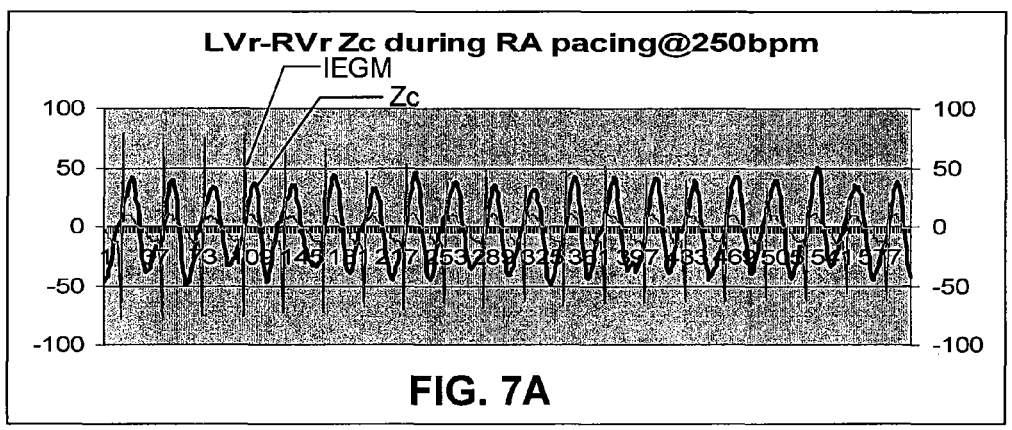
FIG. 7A illustrates the morphology of an exemplary cardiogenic impedance signal obtained during a simulated atrial tachycardia.
Figure 7B:
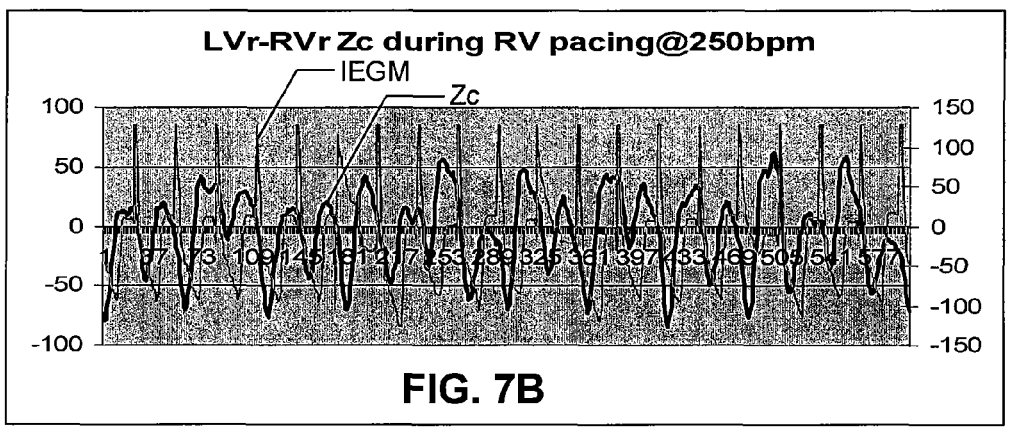
FIG. 7B illustrates the morphology of an exemplary cardiogenic impedance signal obtained during a simulated ventricular tachycardia.

The graph of FIG. 7A illustrates an exemplary intracardiac electrogram (IEGM) signal and a corresponding exemplary cardiogenic impedance (Zc) signal obtained for a animal subject having their right atrium paced at 250 bpm, to simulate SVT. In contrast, FIG. 7B illustrates an IEGM signal and a corresponding Zc signal when the same animal subject's right ventricle was paced at 250 bpm, to simulate VT. The same sensing vector, including a left ventricular ring electrode and a right ventricular ring electrode, was used to obtain the Zc signals in FIGS. 7A and 7B. At step 602, a template representative of a portion (e.g., cycle) of the Zc signal of FIG. 7A can be stored and/or a template representative of a portion of the Zc signal of FIG. 7B can be stored, and a Zc signal obtained at step 304 using the same sensing vector can be compared to such template(s) to determine one or more similarity metric at step 606.

In specific embodiments, one or more cardiogenic impedance signal template indicative of SVT is stored. If a patient's heart rate exceeds a specified threshold, e.g., 150 bpm, and the similarity metric(s) determined at step 606 are indicative of a high similarity with the SVT template(s), then the patient can be diagnosed as experiencing SVT, which typically does not require any cardiac therapy (e.g., at step 610). If a patient's heart rate exceeds a specified threshold, e.g., 150 bpm, and the similarity metric(s) determined at step 606 are indicative of a low similarity with the SVT template(s), then the patient can be diagnosed as experiencing VT, which typically does require cardiac therapy (e.g., at step 610). Alternatively, since the morphology of a cardiogenic impedance signal during normal sinus rhythm and during SVT will be similar, the above can be performed using a normal sinus rhythm template(s) in place of the SVT template(s).

Instead of storing cardiogenic impedance signal template (s) indicative of SVT, or in addition thereto, one or more cardiogenic impedance signal template indicative of VT can be stored. If a patient's heart rate exceeds a specified threshold, e.g., 150 bpm, and an obtained Zc signal(s) is/are similar to the VT template(s), or more similar to the VT template(s) than to the SVT template(s), than it can be determined that a patient is experiencing VT at step 608, and an appropriate therapy (e.g., anti-tachycardia pacing) can be delivered at step 610. If a patient's heart rate exceeds a specified threshold, e.g., 150 bpm, and an obtained Zc signal(s) is/are similar to the SVT template(s), or more similar to the SVT template(s) than to the VT template(s), than it can be determined that a patient is experiencing SVT at step 608. If a patient's heart rate exceeds a specified threshold, e.g., 200 bpm, and the obtained Zc signal(s) is/are not similar to the VT template(s) or the SVT template(s), such information may be used in diagnosing that a patient is experiencing ventricular fibrillation (VF), and cardioversion and/or defibrillation shock therapy can be delivered (e.g., at step 610). It's also possible to obtain VF template(s) during defibrillation threshold (DFT) testing, and to compare obtained Zc signals(s) to such VF template(s), to determine whether a patient is experiencing VF. For example, if a patient's heart rate exceeds a specified threshold, e.g., 200 bpm, and the obtained Zc signal(s) is/are similar to the VF template(s), such information may be used in diagnosing that a patient is experiencing ventricular fibrillation (VF), and cardioversion and/or defibrillation shock therapy can be delivered (e.g., at step 610). Patient and/or physician alerts can also be triggered, in response to specific arrhythmia detections.

As was mentioned above, SVT template(s) can be obtained by pacing a patient's atrium at a relatively high rate, and VT template(s) can be obtained by pacing a patient's ventricle at a relatively high rate. Templates can alternatively be obtained from cardiogenic impedance signals that were obtained during a known detection of an arrhythmia. Templates indicative of other arrhythmias, besides SVT and VT, can also be obtained and stored, and compared to obtained cardiogenic impedance signals for the purpose of detecting an arrhythmia and/or performing arrhythmia discrimination. Alternatively, or additionally, cardiogenic impedance signal template(s) stored at step 602 can be indicative of a patient's normal sinus rhythm. If similarity metric(s) obtained at step 606 indicate that the signal(s) obtained at step 304 is/are most similar to a patient's normal sinus rhythm, then there can be a determination that no arrhythmia is being detected.

In accordance with other embodiments of the present invention, arrhythmia detection and/or discrimination can be performed based on the morphology of one or more obtained cardiogenic impedance signal, without the use of template comparisons. For example, in such embodiments, certain features of morphologies can be monitored for, such as notches or the like, and arrhythmias can be detected based on the presence of certain morphologic features that have been identified as being indicative of specific arrhythmias. The morphology monitoring or matching can include one or more heart beats. The morphologic features, indicative of specific arrhythmias, can be programmed by a physician and/or autonomously determined by an implantable device (e.g., 100). Additionally, such features can be updated with information acquired from the patient.

The above describe arrhythmia detection and arrhythmia discrimination embodiments can be used together with detection and discrimination algorithms that rely on electrocardiogram information, which are known in the art, or they can be used on their own.

It is also noted that multiple sensing vectors can be used to obtain multiple cardiogenic impedance signals, and the morphology of each cardiogenic impedance signal can be compared to the morphology of one or more corresponding template. For example, an atrial sensing vector can be used to obtain an atrial cardiogenic impedance signal that is compared to the morphology of an atrial cardiogenic impedance template, and a ventricular sensing vector can be used to obtain an ventricular cardiogenic impedance signal that is compared to the morphology of a ventricular cardiogenic impedance template. Similarity metrics that are determined based on such comparisons can be used for arrhythmia detection and discrimination. Detection and discrimination rules can take into account, which comparisons result in which similarity metrics.

Figure 8:
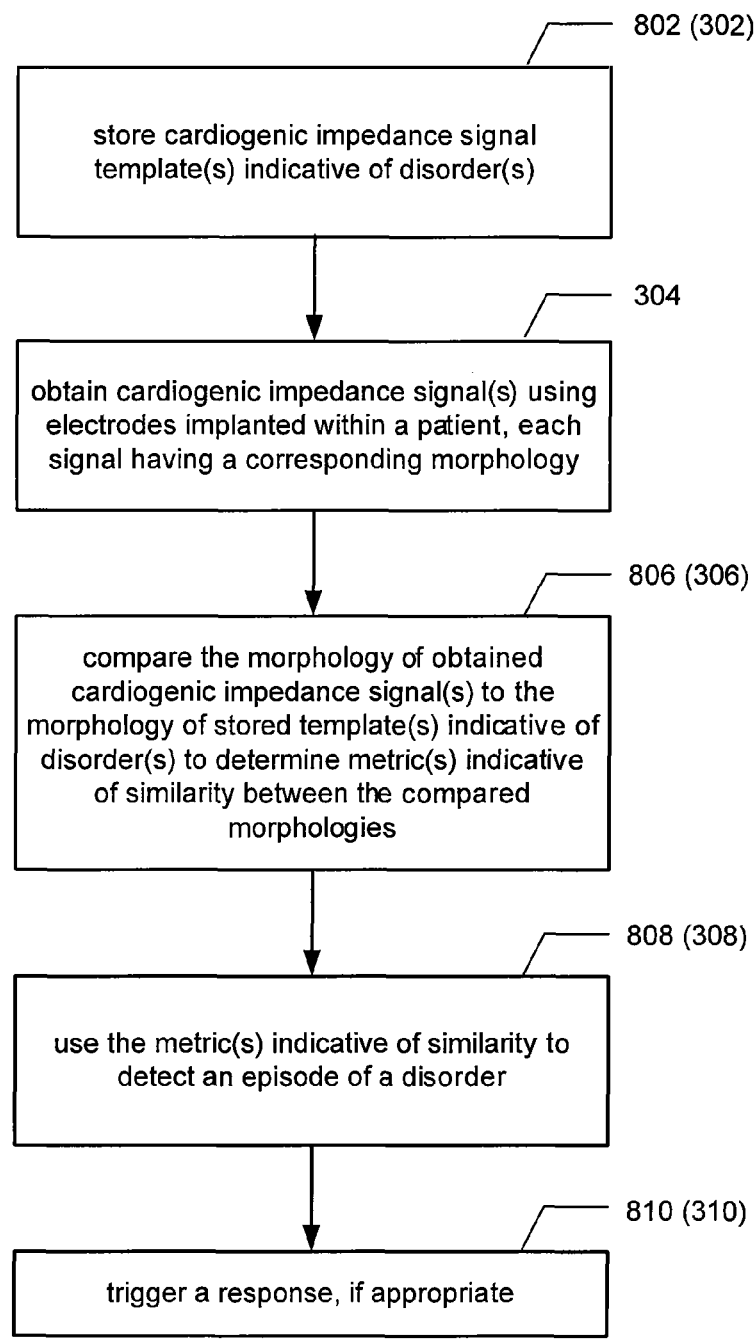
FIG. 8 is a high level flow diagram that is used to explain specific embodiments of the present invention, which are used to detect a disorder.

Embodiments of the present invention can also be used to detect episodes of disorders that affect cardiogenic impedance signals, e.g., to detect episodes of myocardial ischemia, as will now be explained with reference to the high level flow diagram of FIG. 8. Referring to FIG. 8, at step 802, which is an embodiment of step 302, cardiogenic impedance signal template(s) indicative of an episode of one or more disorder is stored. At step 304, one or more cardiogenic impedance signal is obtained, as was explained above in the discussion of FIG. 3. At step 806, one or more similarity metric is determined, based on comparison(s) of template(s) to obtained cardiogenic impedance signal(s), in similar manners as were discussed above. At step 808, the similarity metric(s) is/are used to determine whether an episode of a disorder is detected. At step 810, an appropriate response can be triggered in response to a detected episode of a disorder.

Step 802 can include storing one or more cardiogenic impedance signal template for each of a plurality of different disorders. In such embodiments, step 806 can include determining a plurality of metrics, each of which is indicative of similarity between the morphology of the obtained signal and the morphology of a different one of the templates. At step 808, a detection can be made based on the plurality of metrics. Episodes of disorders can be detected in this manner, so long as a meaningful cardiogenic impedance signal template can be obtained and stored for such other disorders (i.e., so long as episodes of disorders cause a recognizable change in cardiogenic impedance). Other disorders that can be detected in this manner include, but are not limited to, left bundle branch block (LBBB) and right bundle branch block (RBBB).

Figure 9:
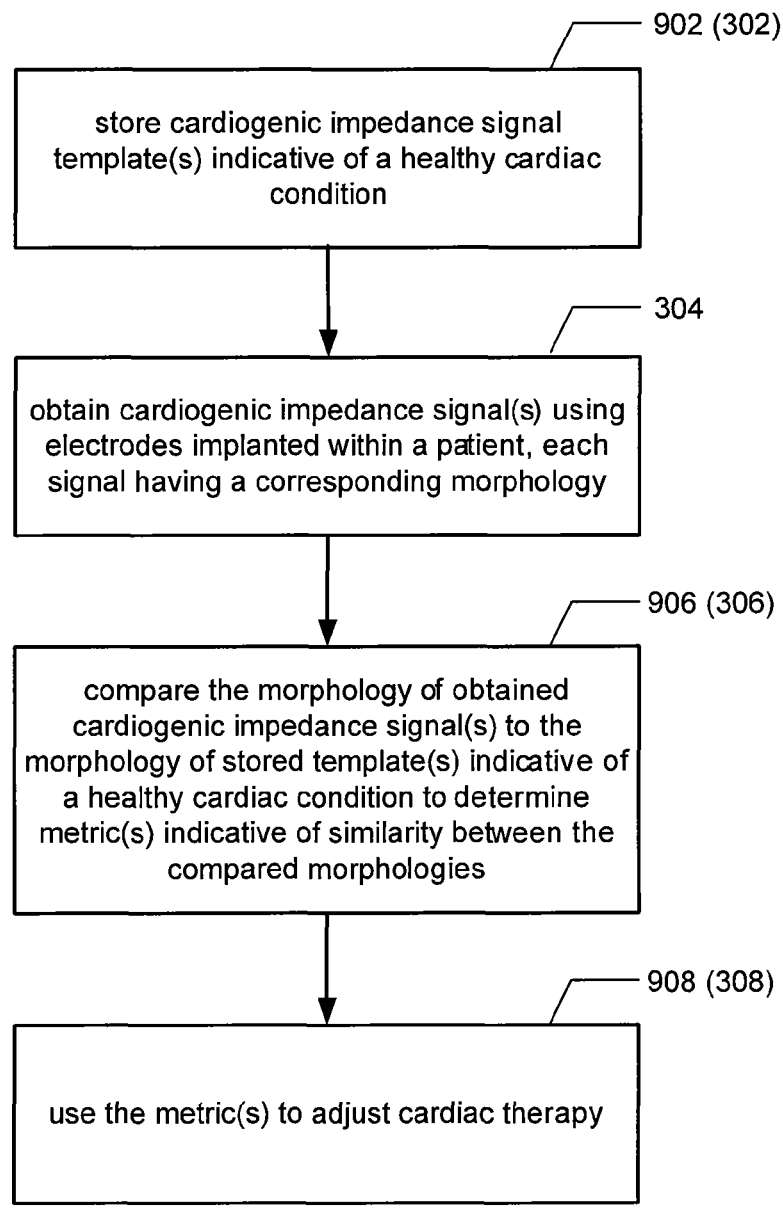
FIG. 9 is a high level flow diagram that is used to explain specific embodiments of the present invention, which are used to adjust cardiac treatment therapy.

Embodiments of the present invention can also be used to adjust treatment therapy, as will now be explained with reference to the high level flow diagram of FIG. 9. Referring to FIG. 9, at step 902, which is an embodiment of step 302, cardiogenic impedance signal template(s) indicative of a healthy cardiac condition is stored. At step 304, one or more cardiogenic impedance signal is obtained, as was explained above in the discussion of FIG. 3. At step 906, one or more similarity metric is determined, based on comparison(s) of template(s) to obtained cardiogenic impedance signal(s), in similar manners as were discussed above. At step 908, one or more cardiac resynchronization (CRT) parameter can be adjusted based on the similarity metric(s). Exemplary CRT parameters, include, but are not limited to, RR interval, atrioventricular (RA-RV) delay, interventricular (RV-LV) delay, interatrial (RA-LA) delay and intraventricular ($RV_1$-$RV_2$ or $LV_1$-$LV_2$) delay. Other exemplary CRT parameters, that can be adjusted, include pacing pulse amplitudes, polarity, waveforms and/or pacing electrode configurations (e.g., pacing vectors and/or pacing locations). In accordance with specific embodiments, CRT parameters are adjusted to attempt to get the patient's cardiogenic impedance signal(s) (obtained at step 304) to be similar to the stored template(s) indicative of a healthy heart. A single CRT parameter can be adjusted at a time, or multiple CRT parameters can be adjusted at the same time, as desired. Additionally, or alternatively, at step 908 drug therapy can be initiation, stopped and/or adjusted based on the similarity metric(s), e.g., to attempt to get the patient's cardiogenic impedance signal(s) (obtained at step 304) to be similar to the stored template(s) indicative of a healthy heart. Additionally, as steps 304 and 906 are repeated over time, changes in the patient's cardiac condition can be determined based on changes in the similarity metric(s) over time.

For completeness, FIG. 10 shows an exemplary impedance measurement circuit architecture 1000 (e.g., which can be used to implement block 278 on FIG. 2), including filter components to obtain raw, cardiogenic, and respiratory impedances. The illustrated architecture 1000 is just one example configuration, other configurations are also possible. In one implementation, the exemplary impedance measurement architecture 1000 includes a pulse generator 1002 for generating an exemplary pulse waveform, in this case a current waveform 1003, for application to the bodily tissue of a patient 1004 and a sensed signal processor 1006 for processing resulting waveforms detected in the tissue, in this case voltage waveforms 1007. An injection (e.g., current pulse) multiplexor 1008 implements the single- or multi-vector aspect of signal application by determining a first set of electrodes for injecting the exemplary waveform 1003. The selection of electrodes may be determined by the vector engine 238 (FIG. 2). Likewise, a sensing (voltage measurement) multiplexer 1010 implements signal sensing by determining a second set of electrodes for sensing the resulting voltage waveforms 1007. The set of sensing electrodes may also be determined, e.g., by the vector engine 238 (FIG. 2). Both the injection multiplexor 1008 and the sensing multiplexor 1010 may be implemented in an implantable device 100 in the electrode configuration switch 226 (FIG. 2).

A waveform 1003 for application to bodily tissue that is generated by the exemplary impedance measurement circuit architecture 1000 posseses many special waveform features and electrical characteristics that are well suited for probing and measuring many types of physiological parameters in the body using current modulated or voltage modulated pulses. Such waveforms are described, as introduced above, in U.S. patent application Ser. No. 11/684,664, entitled "Tissue Characterization Using Intracardiac Impedances with an Implantable Lead System", (Wong et al), filed Mar. 12, 2007, and incorporated herein by reference. Exemplary waveforms 1003 are multi-phasic, with negative phases (pulse segments below baseline) that balance positive phases (pulse segments above baseline). The illustrated waveform 1003 is tri-phasic. Other versions of the waveform 1003 may have more than three phases, may be synchronous or asynchronous, may be rectangular or sinusoidal, etc. One version of the waveform 1003 uses the sinc(x) sampling waveform. In one variation, the exemplary impedance measurement architecture applies the waveform 1003 as a voltage waveform instead of a current waveform and senses the results as electrical current instead of voltage.

Properties of the exemplary waveforms 1003 include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces.

Each waveform 1003 preferably has a total duration less than the charging time constant of the electrode-electrolyte interfaces used to inject and sense the signals. These time constants are typically in the range of a few milliseconds. In one implementation, the duration of waveform 1003 is less than 1 millisecond. This waveform feature is helpful for minimizing polarization effects at these electrode-electrolyte interfaces. Other features of the exemplary waveforms 1003 include symmetric or asymmetric phase duration, decreasing phase amplitudes, and alternating phase signs. Each waveform 1003 typically has null durations in between phases to provide time to allow complete processing of information caused by one phase before the next phase of the waveform 1003 begins. Implementations of the waveform 1003 that have near perfect square wave pulses (or rectangular wave pulses) contain a great deal of high-frequency content. Near-sinusoidal implementations of the waveform 1003 may contain less high frequency content than the rectangular wave versions.

The features of exemplary waveforms 1003 just enumerated provide numerous advantages, including: eliminating the need for fast digital sampling, minimizing artifacts introduced in the measurement process, increased tolerance of small phase delays between injected and sensed signals. The exemplary waveforms 1003 also lend themselves to CMOS realization using low-value switched capacitor solutions. Further, the wide frequency spectrum of the injected signal can be used to implement algorithms that differentiate tissues based on their frequency response, and/or phase delay. The very low duty-cycle of the exemplary waveforms 1003 make them safer for patients. The reduced duty-cycle brings the injected charge and the root-mean-square value of the injected signal well below levels that could be perceived by the patient or that could induce adverse events.

It is noted that the net-zero voltage feature, also referred to as the voltage-balanced feature, refers to the voltage formed on blocking capacitors that appear in series with the load. The flow of current through these capacitors builds up voltage across them. Since these capacitors, such as capacitor 1040 in FIG. 10, also appear in circuits that are responsible for sensing cardiac activity, it is important that the net voltage built up on them be zero. As a result of the net-zero voltage feature, the influence of an exemplary waveform 1003 on the circuits that sense cardiac activity is minimal.

Other features of the exemplary waveforms 1003 derive from the above-mentioned null segments—intra-waveform segments containing no signal—that serve several purposes. First, the null segments allow the electronics in processing circuits to settle during measurement of phases and second, they allow multiple instances of the waveform 1003 to exist in the patient's tissue simultaneously, being staggered by time multiplexing such that a phase of one waveform can be measured during the time that there is no signal between phases of another waveform.

In one implementation, the exemplary waveform 1003 is used to derive physiological measurements based on intracardiac impedances. Based on such cardiogenic impedance measurements, many physiological variables can be trended to detect changes in a patient's condition, such as congestive heart failure (CHF) index, pulmonary edema, systolic slope, contraction (e.g., dZ/dt(max)), diastolic slope, relaxation (e.g., dZ/dt(min)), pre-ejection period (in low resolution), ejection time, left ventricular ejection fraction (LVEF), diastolic heart failure index (DHFI), cardiac index, etc.

The exemplary waveform 1003 provides an elegant and reliable vehicle for measuring bodily impedances in a manner that gives reliably reproducible results. Instead of a conventional technique of trying to sense an instantaneous "snapshot" measurement of a conventionally injected signal, the impedance measurement circuit architecture 1000 derives an impedance measurement by dividing the area under the sensed voltage curve (waveform 1007) by the area of the injected current waveform 1003. An exemplary implantable device 100 can perform this exemplary method by "integrating the curve" of an absolute value of waveforms 1003 or 1007. Sometimes the exemplary implantable device can closely approximate this integration without having to perform an integration operation by directly measuring and summing the area "under" the curve (e.g., under the rectangular wave) of the waveform 1003, that is, the area composed of the absolute value of the three areas of the three phases of an exemplary tri-phasic waveform 1003.

Likewise, the exemplary implantable device can integrate, or closely approximate the integration, by measuring and summing the area "under" the curve (e.g., the rectangular wave) of the waveform 1007, that is, the area composed of the absolute value of the three areas of the three phases. In one implementation, the area of the sensed voltage, waveform 1007, is measured at the output of an integrator circuit. The area of the injected current, waveform 1003, is computed by, or preset by, the micro-controller driving the implantable device. An implantable device 100 may thus use this area-based ("areal") approach to deriving a network of impedance measurements over a multi-vector network.

Returning to description of the impedance measurement circuit architecture 1000 itself, the sensed signal processor 1006 typically consists of pre-amplification circuitry, switched capacitor filters, and an analog to digital converter 1012. In one implementation, the voltage signal from the voltage measurement multiplexer 1010 is processed by several voltage measurement lines or paths. The illustrated sensed signal processor 1006 is able to obtain at least the three different impedance signals introduced above with respect to FIG. 10, that is, low frequency raw impedance $Z_o$ 1013, respiration impedance $Z_r$ 1015, and cardiogenic impedance $Z_c$ 1017. Each measurement can be activated separately or simultaneously.

A digital form of raw impedance $Z_o$ 1013 may be obtained. First, the sensed signal, i.e., the tri-phasic voltage waveform 1007 from the voltage measurement multiplexer 1010, is sent to a preamplifier 1014. The next stage is embodied in a sign conversion and integration module 1016. At this stage, the signal is converted into an absolute value and then integrated over time. Using the integration process instead of conventional instantaneous "snapshot" measurements of impedance components such as pure resistance produces results that are more noise-free and more accurate than the conventional techniques.

The signal is then applied to a discrete-to-continuous signal conversion module 1018. At this point in the architecture 1000, the signals for low frequency impedance $Z_o$ 1013, respiration impedance $Z_r$ 1015, and cardiogenic impedance $Z_c$ 1017 are extracted separately by different filter paths, as summarized in FIG. 10. To obtain the low frequency impedance $Z_o$ 1013, the signal is sent to a level shift and low pass filter module 1020, and then to the analog to digital converter 1012.

A digital form of the respiration impedance $Z_r$ 1015 may be obtained by tapping the analog signal from the input of the level shift and low pass filter module 1020, and feeding the signal to a line consisting of bandpass filters 1022 and 1024 and a low pass filter 1026. The signal is then fed to the analog to digital converter 1012 to obtain digital $Z_r$ 1015.

A digital form of the cardiogenic impedance $Z_c$ 1017 may likewise be obtained by tapping the analog signal from the input of the level shift and low pass filter module 1020, and feeding the signal to a line consisting of high pass filters 1028 and 1030 and a low pass filter 1032. The signal is then fed to the analog to digital converter 1012 to obtain digital $Z_c$ 1017.

In one implementation, the pulse generator 1002 consists of two timing controlled current generators 1034 and 1036 with programmable magnitude. The first current generator 1034 sources current, the other current generator 1036 sinks the current. As part of the charge and voltage balancing process, the switch $SW_{Balance}$ 1038 is used to discharge the external capacitor Cap_Impulse 1040 after each generated impulse. The pulse rate is programmable.

Components of the impedance measurement architecture 1000 may be distributed across the impedance measuring & processing circuits 478 (FIG. 4) and the impedance processing module 440 (FIG. 4), the distribution of components depending on implementation. That is, the exemplary impedance measurement architecture 1000 may be implemented in hardware, software, or combinations thereof. For example, the exemplary impedance measurement architecture 1000 may be implemented in hardware as part of the microcontroller 421 and/or as hardware integrated into the fabric of the exemplary implantable device 100; or as software/firmware instructions programmed into an implementation of the implantable device 100 and executed on the microcontroller 421 during certain modes of operation.

In one implementation, the preamplifier 1014 is included in the impedance measuring & processing circuits 478. The pulse generator 1002 can be implemented in the impedance processing module 440 as may some of the other components of the sensed signal processor 1006.

Although the illustrated version of the impedance measurement circuit architecture 1000 applies a current pulse waveform 1003 and senses a voltage pulse waveform 1007, other implementations can inject a voltage waveform and sense a current waveform.

The "raw" impedance measurement, $Z_o$ 1013, can be useful for determining extra- or intra-cardiac impedances and examining conditions such as pulmonary edema. The respiration component of impedance, $Z_r$ 1015, can be useful for tracking respiration rate and depth, sleep apnea, and other related CHF conditions. The cardiogenic component of impedance, $Z_c$ 1017, can be separated out for tracking various hemodynamic parameters. Additionally, the cardiogenic component of impedance, $Z_c$ 1017, can be used in the various embodiments of the invention described in detail above with reference to FIGS. 3-9.

FIG. 11 illustrates exemplary raw, cardiogenic and respiration impedance signals that can be produced using the circuit of FIG. 10. As explained above, the cardiogenic and respiration impedance components represents variations about the reference line provided by the raw impedance signal. These variations are shown as signed impedance (e.g. positive or negative deflections from raw impedance values) and relate to effects of cardiac contractility and respiratory cycle, respectively.

It is noted that the term "based on", as used herein, means based at least in part on, unless stated otherwise. It is also noted that when a similarity metric, or the like, "is used" in a determination or analysis, other metrics and/or factors can also be used. For example, where a similarity metric is used to detect an arrhythmia, it is possible, and likely, that a measure of the patient's heart rate is also used in such a determination. Accordingly, embodiments of the present invention are intended to encompass the use of additional metrics and factors, when determinations, analysis, and/or adjustments are performed, unless stated otherwise.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 3, 4, 6, 8 and 9. Further, it is possible to change the order of some of the steps shown in FIGS. 3, 4, 6, 8 and 9, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method, comprising:
   (a) storing a plurality of cardiogenic impedance signal templates, wherein each template has a corresponding morphology and is associated with one of a plurality of sensing vectors;
   (b) obtaining a plurality of cardiogenic impedance signals, each cardiogenic signal associated with a different one of the plurality of sensing vectors, wherein each signal has a corresponding morphology;
   (c) comparing the morphology of each obtained cardiogenic impedance signal to the morphology of one of the plurality of stored templates having a same associated sensing vector to determine a plurality of metrics indicative of similarity between the compared morphologies;
   (d) combining the plurality of metrics indicative of similarity into a single similarity score; and
   (e) using the single similarity score to analyze the patient's heart failure condition and/or to adjust heart failure treatment therapy, wherein the patient's heart failure condition that is analyzed does not include arrhythmias and wherein the heart failure treatment therapy does not include an arrhythmia treatment therapy.

2. The method of claim 1, wherein:
   step (a) includes storing a plurality of cardiogenic impedance signal templates indicative of a heart failure condition, wherein each template has a corresponding morphology and is associated with one of a plurality of sensing vectors;
   step (c) includes determining a plurality of metrics indicative of similarity between the morphology of each obtained cardiogenic impedance signal and the morphology of one of the plurality of stored templates indicative of the heart failure condition having a same associated sensing vector; and
   step (e) comprises determining a change in the patient's heart failure condition based on the single similarity score.

3. The method of claim 2, wherein step (e) includes monitoring for an onset of heart failure based on the single similarity score; and further comprising:
   (f) triggering an alert in response to detecting an onset of heart failure.

4. The method of claim 1, wherein:
   step (a) includes, for each of a plurality of different heart failure conditions, storing a plurality of cardiogenic impedance signal templates, wherein each template has a corresponding morphology, and is associated with one of a plurality of sensing vectors;
   step (c) includes, for each of the different heart failure conditions, determining a plurality of metrics indicative of similarity between the morphology of each obtained signal and the morphology of one of the plurality of stored templates having a same associated sensing vector;
   step (d) includes, for each of the different heart failure conditions, combining the plurality of metrics indicative of similarity into a single similarity score corresponding to the heart failure condition; and
   step (e) includes using results of step (d) to determine the patient's heart failure condition.

5. The method of claim 1, wherein step (a) includes:
   obtaining a plurality of cardiogenic impedance signal templates indicative of an initial heart failure condition, wherein each template has a corresponding morphology and is associated with one of a plurality of sensing vectors; and
   storing each said template indicative of the initial heart failure condition.

6. The method of claim 1, wherein:
   step (a) includes storing a plurality of cardiogenic impedance signal templates indicative of an initial heart failure condition, wherein each template has a corresponding morphology and is associated with one of a plurality of sensing vectors;
   step (c) includes determining a plurality of metrics indicative of similarity between the morphology of each obtained cardiogenic impedance signal and the morphology of one of the plurality of stored templates indicative of the initial heart failure condition having a same associated sensing vector; and
   step (e) comprises determining a change in the patient's heart failure condition based on the single similarity score.

7. The method of claim 1, further comprising repeating steps (b) and (c) over time, and monitoring changes in the patient's heart failure condition based on changes in the metric over time.

8. The method of claim 1, wherein:
   step (a) includes storing a plurality of cardiogenic impedance signal templates indicative of a healthy cardiac condition, wherein each template has a corresponding morphology and is associated with one of a plurality of sensing vectors;

step (c) includes determining a plurality of metrics indicative of similarity between the morphology of each obtained cardiogenic impedance signal and the morphology of one of the plurality of stored templates indicative of the healthy cardiac condition having a same associated sensing vector; and step (e) comprises adjusting heart failure treatment therapy based on the single similarity score, to attempt to increase the single similarity score.

* * * * *